US009541509B2

(12) United States Patent
Akahori et al.

(10) Patent No.: US 9,541,509 B2
(45) Date of Patent: Jan. 10, 2017

(54) RADIATION IMAGING APPARATUS, RADIATION IMAGING METHOD, BODY MOVEMENT MEASURING METHOD, AND BODY MOVEMENT MEASURING PROGRAM

(75) Inventors: Sadato Akahori, Kanagawa-ken (JP); Yoshitaka Yamaguchi, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 466 days.

(21) Appl. No.: 13/637,553

(22) PCT Filed: Mar. 28, 2011

(86) PCT No.: PCT/JP2011/001836

§ 371 (c)(1), (2), (4) Date: Dec. 10, 2012

(87) PCT Pub. No.: WO2011/118236

PCT Pub. Date: Sep. 29, 2011

(65) Prior Publication Data

US 2013/0077749 A1 Mar. 28, 2013

(30) Foreign Application Priority Data

Mar. 26, 2010 (JP) ................................ 2010-071586
Mar. 29, 2010 (JP) ................................ 2010-074023

(51) Int. Cl.
*A61B 6/00* (2006.01)
*G01N 23/04* (2006.01)
*A61B 6/02* (2006.01)

(52) U.S. Cl.
CPC ............... *G01N 23/04* (2013.01); *A61B 6/486* (2013.01); *A61B 6/487* (2013.01); *A61B 6/527* (2013.01);

(Continued)

(58) Field of Classification Search
USPC ........................................................ 378/98.12
See application file for complete search history.

(56) References Cited

U.S. PATENT DOCUMENTS 6,196,715 B1 * 3/2001 Nambu .................... A61B 6/00 378/11
6,546,068 B1 4/2003 Shimura
(Continued)

FOREIGN PATENT DOCUMENTS

JP 9-56707 A 3/1997
JP 10-201864 A 8/1998
(Continued)

OTHER PUBLICATIONS

Communication dated Aug. 26, 2014 from the State Intellectual Office of People's Republic of China in counterpart application No. 201180016117.3.

(Continued)

*Primary Examiner* — Phillip A Johnston
(74) *Attorney, Agent, or Firm* — Sughrue Mion, PLLC

(57) ABSTRACT

A radiation detector is moved along a predetermined axis of movement. Radiation which has passed through a subject is irradiated onto the radiation detector each time the position of the radiation detector changes due to the movement. Signals are read out from the radiation detector each time that radiation is irradiated, to obtain a plurality of radiation images of the subject. Mechanical errors of the radiation detector are detected at each imaging operation, and mechanical error corrected images in which the mechanical errors are corrected are obtained. Amounts of shift of the subject among the mechanical error corrected images are detected, and amounts of movement of the subject during imaging operations are detected based on the amounts of shift.

19 Claims, 21 Drawing Sheets

(52) U.S. Cl.
CPC ............. *A61B 6/5264* (2013.01); *A61B 6/584* (2013.01); *A61B 6/025* (2013.01); *A61B 6/4452* (2013.01); *A61B 6/5241* (2013.01); *A61B 6/582* (2013.01)

(56) References Cited

U.S. PATENT DOCUMENTS

| | | | | |
|---|---|---|---|---|
| 7,412,023 | B2 * | 8/2008 | Ohishi | A61B 6/4233 378/4 |
| 7,986,769 | B2 * | 7/2011 | Kotani | A61B 6/00 378/62 |
| 8,552,392 | B2 * | 10/2013 | Kito et al. | 250/370.09 |
| 2003/0142787 | A1 | 7/2003 | Jabri et al. | |
| 2004/0252811 | A1 | 12/2004 | Morita et al. | |
| 2007/0071171 | A1 | 3/2007 | Hayashida et al. | |
| 2010/0067773 | A1 * | 3/2010 | Yamaguchi | G06T 7/0042 382/132 |

FOREIGN PATENT DOCUMENTS

| | | | |
|---|---|---|---|
| JP | 2000-152926 | A | 6/2000 |
| JP | 2000-201920 | A | 7/2000 |
| JP | 2003-244542 | A | 8/2003 |
| JP | 2005-21675 | A | 1/2005 |
| JP | 2005-296340 | A | 10/2005 |
| JP | 2007-82907 | A | 4/2007 |
| JP | 2007-330278 | A | 12/2007 |
| JP | 2009-200423 | A | 9/2009 |
| JP | 2009-240656 | A | 10/2009 |
| JP | 2010-94498 | A | 4/2010 |

OTHER PUBLICATIONS

Extented European Search Report dated Aug. 23, 2013, issued in European Patent Application No. 11759045.5.

F. Yamaguchi, "Geographic Processing Engineering", Nikkan Kogyo Shimbun Press, 1981, pp. 73-75.

International Search Report for PCT/JP2011/001836 dated Jun. 28, 2011.

Communication dated May 13, 2014 from the European Patent Office in counterpart European Patent Application No. 11759045.5.

* cited by examiner 150
20
21
22
110
102
N
N1
N2
N3
N4
104
Cr
25
26
27
28
100
111
112
X
Y
Z
5E
5F
Q1
Q2
Q3
Q4
34
35
36
37
38
39
60
80
81
82
83
84
90
91
92
93
94
95
EP
CP
30
70 a b

M1 M2

W$_2$

M1 M2

M1 M2

M1 M2

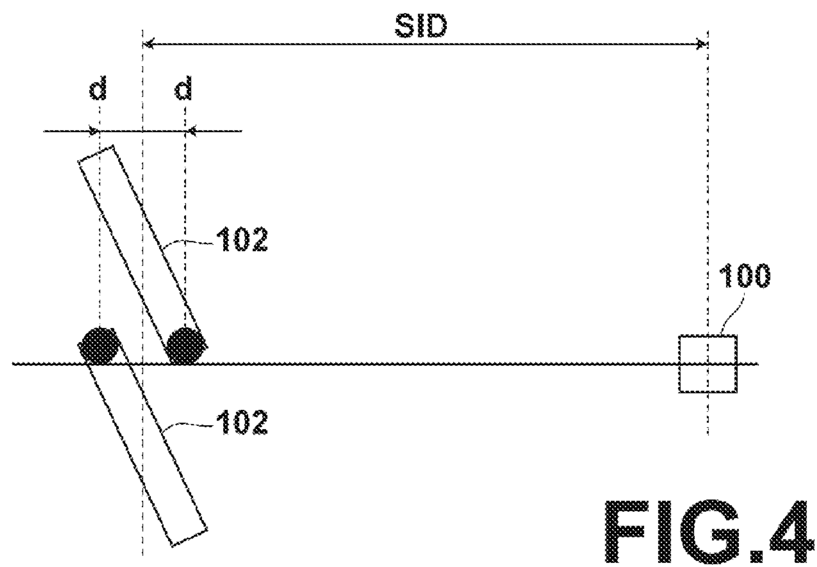
FIG.4
FIG.5
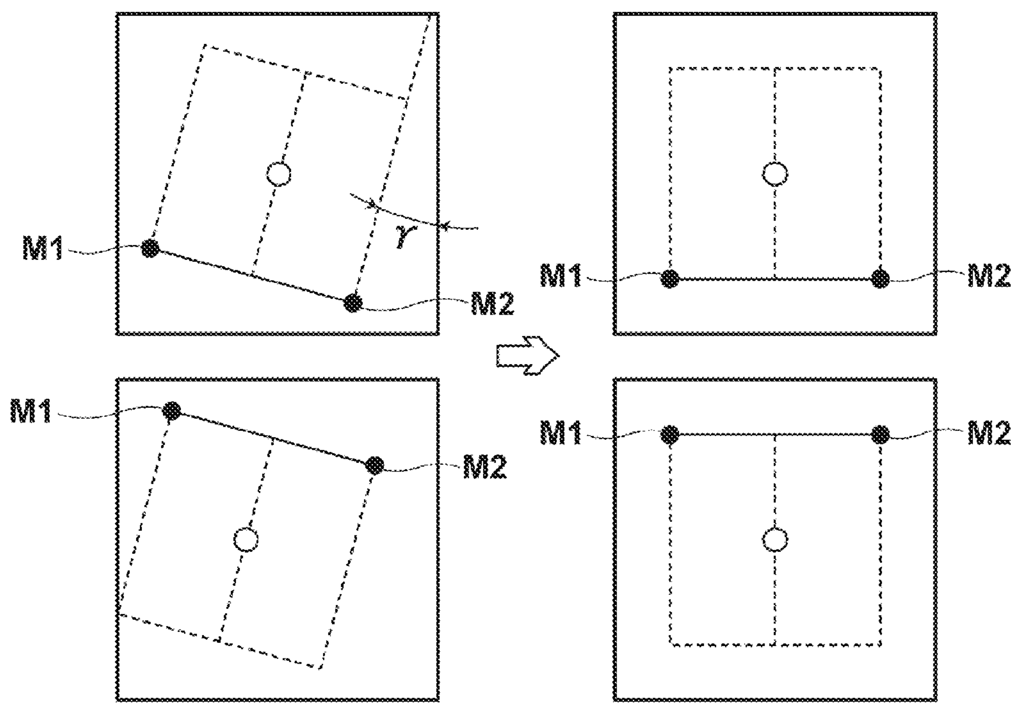

S1
T
K
K
I
S2

S1
T1
T3
T2
T4
K
K
I1
I3
I2
I4
S2 a
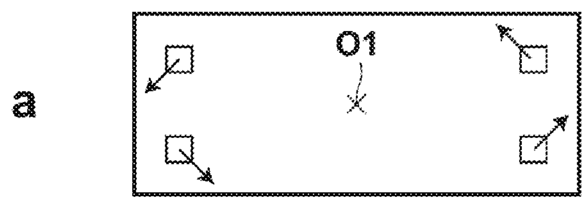
b
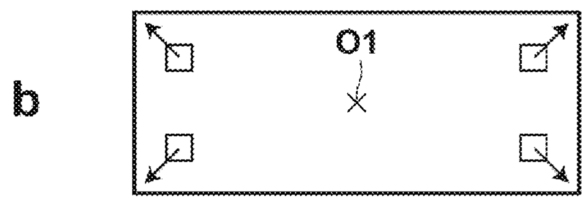
FIG.24
c
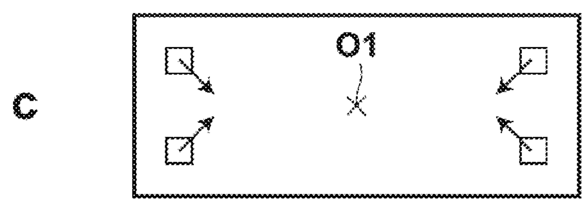
d
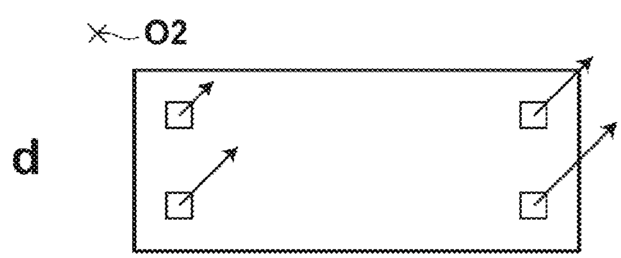
FIG.25
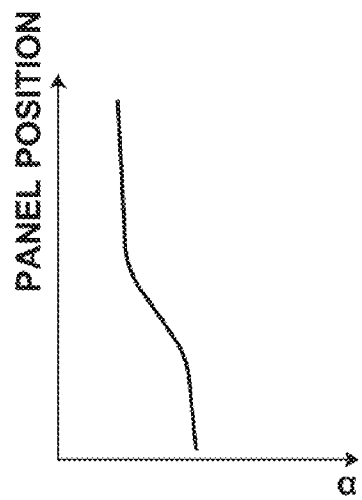

210
MEMORY SECTION
226
DISPLAY SECTION
225
OPERATING SECTION
224
CALCULATING SECTION
228
REGION OF INTEREST SETTING SECTION
232
CONTROL SECTION
234
RECONSTRUCTING SECTION
222
IMAGE OBTAINING SECTION
220
SELECTING SECTION
230
MOVING MECHANISM
216
MOVING MECHANISM
218
A
212
206
202
204
214
B

Sn
S2
S1
212

202
O1
O2
G1
P11
P12
G2
P21
P22
(P21-P11)
Gn
Pn2
Pn1
(Pn1-P11)

RADIATION IMAGING APPARATUS, RADIATION IMAGING METHOD, BODY MOVEMENT MEASURING METHOD, AND BODY MOVEMENT MEASURING PROGRAM

CROSS REFERENCE TO RELATED APPLICATIONS

This application is a National Stage of International Application No. PCT/JP2011/001836 filed Mar. 28, 2011, claiming priority based on Japanese Patent Application Nos. 2010-071586 filed Mar. 26, 2010 and 2010-074023 filed Mar. 29, 2010, the contents of all of which are incorporated herein by reference in their entirety.

TECHNICAL FIELD

The present invention is related to a radiation imaging apparatus that moves a radiation source and/or a radiation detecting means to perform a plurality of imaging operations of a subject, and particularly to detecting body movements of the subject in such an apparatus.

BACKGROUND ART

Conventionally in the medical field and the like, various radiation detectors (so called "Flat Panel Detectors", hereinafter referred to as FPD's) that record radiation images related to subjects when radiation which has passed through the subjects is irradiated thereon have been proposed and are in practical use. Examples of such FPD's include those that utilize semiconductors such as amorphous selenium that generate electrical charges when irradiated with radiation. FPD's of this type that utilize the so called optical readout method and the TFT readout method have been proposed.

Accompanying the spread of radiation imaging apparatuses that employ the FPD's described above, functions in which a series of imaging operations are performed to obtain a plurality of images, and a combined image is generated from the plurality of images (tomosynthesis imaging, longitudinal imaging, energy subtraction imaging, and CT imaging, as disclosed in Patent Documents 2 and 4, for example) are being focused on. In such imaging operations, there are cases in which patients (subjects) move between imaging operations because there are temporal lags among the imaging operations. If body movements of the subjects occur, there is a problem that the combined image cannot be generated accurately.

In addition, in the imaging functions described above, mechanical errors, such as movement errors of radiation sources and FPD's due to installation errors of apparatuses, deterioration of apparatuses over time, etc., may adversely influence the combining of images separately from body movements of the subjects. Hereinafter, these mechanical errors will be described with longitudinal imaging as an example. First, longitudinal imaging is executed in cases that a possible imaging range is smaller than a target to be imaged. In longitudinal imaging, an FPD is moved along a predetermined axis of movement, and receives irradiation of radiation that has passed through a single subject each time the position of the FPD changes. A readout operation is executed to read out signals from the FPD each time radiation is irradiated (each time that a radiation image is recorded), to obtain image data that represent a radiation image by each readout operation. Then, the image data are combined such that they are linked, and image data that represent an elongate part of a subject can be obtained. Such imaging is generally referred to as longitudinal imaging.

When radiation images are combined as described above, there are cases in which there are shifts at the boundaries of the combined image obtained by combining the radiation images due to inclinations of an imaging surface of an FPD. There are several types of inclinations that cause this problem. Inclinations of imaging surfaces will be described in detail below with reference to FIG. 27 and FIG. 28.

First, a of FIG. 27 is a diagram that schematically illustrates an imaging system for obtaining radiation images, viewed from the side thereof. In FIG. 27, reference numeral 100 denotes a radiation source, reference numeral 101 denotes a stand that guides the movement of a rectangular panel shaped FPD 110, and reference numeral 102 denotes an imaging surface of the FPD 110. Note that in the following description, the subject of images which are recorded is a grating 103 in order to facilitate understanding of the problem. That is, radiation 104 emitted from the radiation source 100 passes through the grating 103 is irradiated onto the imaging surface 102 of the FPD 110. In addition, the rectangular panel shaped FPD 110 is set such that the surface of the panel and an edge of the panel are parallel to the direction in which the stand 101 extends (the direction indicated by arrow A), and is moved along the direction indicated by arrow A. In this case, the direction indicated by arrow A is the axis of movement. Prior to and following movement of the FPD 110, the radiation 104 which has passed through the grating 103 is irradiated onto the FPD 110 in a still state, to obtain a first radiation image and a second radiation image.

As one problem, the imaging surface 102 (that is, a two dimensional matrix of pixel sections that constitute the imaging surface) is inclined by an angle α due to assembly error of the FPD 110. In addition, there are cases in which the FPD 110 itself is provided in an inclined manner with respect to the axis of movement, even in the case that the imaging surface 102 is not inclined within the FPD 110, that is, the matrix that constitutes the imaging surface 102 is formed parallel to the surface and an edge of the rectangular panel shaped FPD 110. If the imaging surface 102 is inclined in this manner, the radiation images of the grating 103 which are obtained by a first imaging operation and a second imaging operation will be those as illustrated as b and c of FIG. 27. That is, if the portion in the vicinity of the lower edge of the first recorded image and the portion in the vicinity of the upper edge of the second recorded image are to be linked by template matching or the like, the lengths of the subject at these portions will differ, and shift will be present at the boundary therebetween.

In this case, the angle of inclination α of the imaging surface 102 is an angle of inclination with respect to the axis of movement which extends in the direction indicated by arrow A, because the FPD 110 is set as described above.

Next, another problem will be described with reference to FIG. 28. a of FIG. 28 is a diagram that schematically illustrates an imaging system for obtaining radiation images, viewed from the front thereof. Note that a radiation source is not shown in FIG. 28, but is arranged so as to irradiate radiation along a direction perpendicular to the drawing sheet. As illustrated in FIG. 28, there are cases in which the imaging surface 102 is inclined by an angle γ with respect to an edge of the panel within a plane parallel to the surface of the panel of the FPD (a plane parallel to the drawing sheet) due to an assembly error of the FPD 110. In addition, there are cases in which the FPD 110 itself is provided in an inclined manner with respect to the axis of movement, even in the case that the imaging surface 102 is not inclined within the FPD 110, that is, the matrix that constitutes the imaging surface 102 is formed parallel to the surface and an edge of the rectangular panel shaped FPD 110. Note that in FIG. 28, a portion of the pixel sections are denoted by reference letter G. If the imaging surface 102 is inclined in this manner, the radiation images of the grating 103 which are obtained by a first imaging operation and a second imaging operation will be those as illustrated as b and c of FIG. 28. That is, if the portion in the vicinity of the lower edge of the first recorded image and the portion in the vicinity of the upper edge of the second recorded image are to be linked by template matching or the like, shifts will be generated at the boundary therebetween.

Note that in this case as well, the angle of inclination $\gamma$ of the imaging surface 102 is an angle of inclination with respect to the axis of movement which extends in the direction indicated by arrow A, because the FPD 110 is set in the same manner as that illustrated in FIG. 27.

In the case that the size of the FPD 110 is 40 cm·40 cm, and the distance (SID) from the radiation source to the imaging surface is 180 cm, the aforementioned shifts at the boundary of the combined image will be approximately 0.5 mm at the end of the image if the angle of inclination $\alpha$ is 0.31 degrees, and approximately 0.5 mm if the angle of inclination $\gamma$ is 0.07 degrees, which are significant shifts.

Cases in which the inclinations of the imaging surface are constant during movement of the FPD have been described above. However, if the imaging surface gradually becomes inclined accompanying movement of the FPD, the inclination of the imaging surface will change accompanying movement of the FPD. Similar problems will occur in such a case as well. FIG. 29 is a diagram that schematically illustrates such a situation. Note that the case illustrated in FIG. 29 is that in which not only inclination of the imaging surface, but also displacement in the horizontal direction occurs accompanying movement of the FPD 110. Such a phenomenon will occur if the precision of a guide mechanism for guiding the movement of the FPD 110 is low, or if a gap between a guide rod and a guiding member that slides along the guide rod, as constituent elements of the guiding mechanism, is set comparatively large.

In such a case, the radiation images of the grating 103 obtained by a first imaging operation and a second imaging operation will be those illustrated as b and c of FIG. 29. In this case as well, if the portion in the vicinity of the lower edge of the first recorded image and the portion in the vicinity of the upper edge of the second recorded image are to be linked by template matching or the like, shifts will be generated at the boundary therebetween.

Further, the problem of shifts being generated at the boundaries among images are not caused only by inclination of the imaging surface, but also in cases that the imaging surface is displaced from a predetermined position during irradiation of radiation. This displacement will be described in detail below.

FIG. 30 is a diagram that schematically illustrates a situation in which displacement of the imaging surface occurs. a of FIG. 30 is a diagram that schematically illustrates an imaging system for obtaining radiation images, viewed from the side thereof. In the case that longitudinal imaging is to be executed, the FPD 110 is to be positioned at predetermined positions during a first imaging operation and a second imaging operation such that the positions overlap to a certain degree along the direction indicated by arrow A. However, if a mechanism for moving the FPD 110 has undergone changes over time, there are cases in which the FPD 110 will be displaced from the predetermined positions in a direction parallel to the direction indicated by arrow A during each irradiation operation. FIG. 30 illustrates a case in which the FPD is displaced downward for a length $\Delta y$ from the predetermined position for the second irradiation operation.

In this case, the radiation images of the grating 103 obtained by the first and second imaging operations will be those as illustrated in b of FIG. 30 and c of FIG. 30. In this case, the images are combined such that the position, within the first image indicated by $y_0$ in the drawing and the upper edge of the second image are matched. However, a shift will be present at the boundary between the images, because the upper edge of the second image is displaced for the length $\Delta y$.

Further, there are cases in which displacement occurs in a direction perpendicular to the direction indicated by arrow A. FIG. 31 is a diagram that schematically illustrates a situation in which such displacement occurs. a of FIG. 31 is a diagram that schematically illustrates an imaging system for obtaining radiation images, viewed from the front thereof. Note that a radiation source is not shown in FIG. 31, but is arranged so as to irradiate radiation along a direction perpendicular to the drawing sheet.

When longitudinal imaging is executed, the FPD 110 is to be placed at predetermined positions which are aligned in the direction perpendicular to the direction indicated by arrow A during a first irradiation operation and a second irradiation operation. However, if a mechanism for moving the FPD 110 has undergone changes over time, or if the stand 101 (more specifically, rails that guide the movement of the FPD 110) is bent as illustrated in FIG. 31, there are cases in which the FPD 110 will be displaced from the predetermined positions in a direction perpendicular to the direction indicated by arrow A during each irradiation operation. FIG. 31 illustrates a case in which the FPD is displaced rightward for a length $\Delta x$ from the predetermined position for the second irradiation operation.

In this case, the radiation images of the grating 103 obtained by the first and second imaging operations will be those as illustrated in b of FIG. 31 and c of FIG. 31. In this case, the images are combined such that the first image and the second image are matched in the horizontal direction, that is, the direction perpendicular to the direction indicated by arrow A. However, a shift will be present at the boundary between the images, because the second image is displaced for the length $\Delta x$.

For these reasons, a technique for correcting shifts at the boundaries within combined images due to inclination of the imaging surface of the FPD and displacement of the FPD from predetermined positions (hereinafter, referred to as mechanical errors of the imaging surface) has been proposed (refer to Patent Document 1).

Meanwhile, there is a possibility that body movements of the subject will occur during longitudinal imaging utilizing an FPD as described above. In the case that body movements occur, it is not possible to appropriate combine a plurality of radiation images, and accurate measurement is hindered. Therefore, it becomes necessary to execute imaging operations repeatedly. For this reason, techniques for detecting body movements of subjects and ceasing imaging operations or issuing warnings indicating that body movements have occurred have been proposed (refer to Patent Documents 2 and 3).

Note that similar errors due to body movement of subjects during imaging operations and problems due to mechanical errors of imaging apparatuses may also occur during tomosynthesis imaging, in which a plurality of images are obtained while moving an FPD and/or a radiation source.

PRIOR ART DOCUMENTS

Patent Documents

[Patent Document 1]

Japanese Patent Application No. 2009-200423

[Patent Document 2]

Japanese Unexamined Patent Publication No. 2007-082907

[Patent Document 3]

Japanese Unexamined Patent Publication No. 2009-240656

[Patent Document 4]

Japanese Unexamined Patent Publication No. 2003-244542

It is possible to correct shifts at the boundaries due to mechanical errors when combining images by employing the technique disclosed in Patent Document 1. However, only shifts due to mechanical errors can be corrected, and shifts at the boundaries due to body movements of subjects will remain. If images are combined in a state in which shifts at the boundaries due to body movements are present, the images cannot be combined accurately.

Combining images by deforming them such that the shifted portions are matched based on the designs of subjects by a technique such as morphing employing a known template matching method or the like may be considered. However, in the case that the template matching method or the like is employed, images will be deformed to correct both shifts due to mechanical errors and shifts due to body movements. Therefore, it will not be possible to confirm whether body movements to a degree that would alter measurement results have occurred from a combined image. As a result, accurate measurements will not be able to be performed employing the combined image.

Examples of possible methods for detecting body movements of a subject include: mounting a sensor that detects body movements of the subject on a radiation imaging apparatus; and detecting body movements of the subject by comparing the positions of the subject within a plurality of obtained images. The latter method of detecting body movements of the subject based on obtained images is preferable, because it is not necessary to provide a separate sensor.

Body movements of the subject can be detected based on obtained images in the case that neither a radiation source nor an FPD is moved, as in energy subtraction imaging operations, by comparing the obtained images (refer to Patent Documents 2 and 4, for example). However, in cases that the positions of radiation sources and FPD's change among obtained images as in tomosynthesis imaging operations, longitudinal imaging operations, and CT imaging operations, it is necessary to take the positions of the radiation sources and the FPD's corresponding to each obtained image into consideration. Because the amounts of movement in the projected positions of subjects within a plurality of obtained images reflect both the movement of the radiation sources and the FPDS and body movements, there is a problem that body movements cannot be isolated and detected correctly.

The present invention has been developed in view of the foregoing circumstances. It is an object of the present invention to enable detection of shifts at the boundaries of images due to movement of subjects in addition to shifts at the boundaries of images due to mechanical errors when combining a plurality of radiation images obtained by lengthwise imaging.

DISCLOSURE OF THE INVENTION

A first imaging apparatus of the present invention comprises:

an imaging means for irradiating radiation;

a radiation detector for detecting the radiation; and a moving means for moving the imaging means and/or the radiation detector;

the radiation imaging apparatus being configured to perform a plurality of imaging operations of a subject by moving the imaging means and/or the radiation detector; and is characterized by further comprising:

image obtaining means for reading out signals from the radiation detector each time that an imaging operation is performed, to obtain a plurality of images of the subject;

a mechanical error detecting means for detecting mechanical errors of the imaging means and/or the radiation detector; and body movement obtaining means for obtaining the amounts of body movement of the subject during the imaging operations, based on the mechanical errors obtained by the mechanical error detecting means.

The first radiation imaging apparatus of the present invention may be additionally characterized by:

the radiation imaging apparatus moving the radiation detector, irradiating radiation which has passed through the subject onto the radiation detector each time that the position of the radiation detector changes by being moved, and obtaining a plurality of radiation images, at least portions thereof being overlapped, and comprising:

an imaging means that moves the radiation detector along a predetermined axis of movement and irradiates radiation which has passed through the subject onto the radiation detector each time that the position of the radiation detector changes due to the movement;

an image obtaining means for reading out signals from the radiation detector each time the radiation detector is moved and the radiation is irradiated, to obtain a plurality of radiation images of the subject;

a mechanical error detecting means for detecting mechanical errors of the radiation detector;

a mechanical error correcting means for correcting the mechanical errors in the plurality of radiation images, to obtain mechanical error corrected radiation images;

a shift detecting means, for detecting amounts of shift in the subject among the mechanical error corrected radiation images; and a body movement obtaining means for obtaining the amounts of body movement of the subject during the imaging operations, based on the amounts of shift.

The first radiation imaging apparatus of the present invention may further comprise:

display means for displaying the amounts of body movement.

The first radiation imaging apparatus of the present invention may further comprise:

a body movement correcting means for correcting the shifts of the subject among the mechanical error corrected radiation images based on the amounts of body movement, to obtain body movement corrected radiation images; and an image combining means for generating body movement corrected combined images, which are the body movement corrected radiation images combined with each other; and the display means may be a means for displaying the body movement corrected combined images.

The first radiation imaging apparatus of the present invention may be further characterized by:

the image combining means generating the body movement corrected combined images such that the degree of positional alignment can be visually confirmed at the portions of the body movement corrected images at which a plurality of the body movement corrected images overlap.

The first radiation imaging apparatus of the present invention may be still further characterized by:

the image combining means further being a means for generating mechanical error corrected combined images, which are the mechanical error corrected radiation images combined with each other; and the display means being a means for switchably displaying the body movement corrected combined images and the mechanical error corrected combined images.

The first radiation imaging apparatus of the present invention may further comprise:

warning means for issuing a warning in the case that the amounts of body movement exceed a predetermined threshold value.

In this case, the imaging means may cease irradiation of the radiation onto the subject when a warning is issued by the warning means.

The warning may be any desired warning, such as an audio warning, a visual warning which is displayed, or a combination of an audio warning and a visual warning.

In the first radiation imaging apparatus of the present invention, the mechanical errors may be at least one of: inclination of an imaging surface, displacement of the imaging surface from a predetermined position, relative shifting among the plurality of radiation images, and displacement of a subject surface, which is a reference surface of the subject, and the imaging surface in a direction parallel thereto.

A radiation imaging method of the present invention performs a plurality of imaging operations of a subject by moving an imaging means that irradiates radiation and/or a radiation detector that detects radiation, and is characterized by comprising the steps of:

reading out signals from the radiation detector each time that an imaging operation is performed, to obtain a plurality of images of the subject;

detecting mechanical errors of the imaging means and/or the radiation detector; and obtaining the amounts of body movement of the subject during the imaging operations, based on the detected mechanical errors.

The radiation imaging of the present invention may be additionally characterized by:

the radiation detector being moved, radiation which has passed through the subject being irradiated onto the radiation detector each time that the position of the radiation detector changes by being moved, and a plurality of radiation images, at least portions thereof being overlapped, being obtained, and comprising the steps of:

moving the radiation detector along a predetermined axis of movement and irradiating radiation which has passed through the subject onto the radiation detector each time that the position of the radiation detector changes due to the movement;

reading out signals from the radiation detector each time the radiation detector is moved and the radiation is irradiated, to obtain a plurality of radiation images of the subject;

detecting mechanical errors of the radiation detector;

correcting the mechanical errors in the plurality of radiation images, to obtain mechanical error corrected radiation images;

detecting amounts of shift in the subject among the mechanical error corrected radiation images; and obtaining the amounts of body movement of the subject during the imaging operations, based on the amounts of shift.

The radiation imaging method of the present invention may be provided as a program that causes a computer to execute the radiation imaging method.

A second radiation imaging apparatus of the present invention comprises:

a radiation source for emitting radiation;

a radiation detecting means for detecting the radiation; and a moving means for moving the radiation source and/or the radiation detector;

the radiation source and/or the radiation detector being moved to perform a plurality of imaging operations of a subject; and is characterized by further comprising:

an imaging system actual movement calculating means, for moving the radiation source and/or the radiation detecting means according to a predetermined pattern, performing a plurality of imaging operations of a reference subject placed at a known position, and for calculating the actual amounts of movement of the radiation source and/or the radiation detecting means based on the projected position of the reference subject within each image obtained by the plurality of imaging operations;

a subject movement specifying means, for specifying the amounts of movement of the subject within a plurality of images, which are obtained by moving the radiation source and/or the radiation detecting means according to the predetermined pattern and performing a plurality of imaging operations;

an estimated subject movement calculating means, for calculating estimated amounts of movement of the subject within a plurality of images which are obtained by moving the radiation source and/or the radiation detecting means according to the predetermined pattern for the actual amounts of movement and performing a plurality of imaging operations; and a body movement evaluation value calculating means, for calculating a body movement evaluation value that indicates the degree of body movement of the subject, based on a difference between the amounts of movement of the subject and the estimated amounts of movement of the subject.

A body movement measuring method of the present invention measures the degree of body movement of a subject, for use in a radiation imaging apparatus comprising a radiation source for emitting radiation, a radiation detecting means for detecting the radiation, and a moving means for moving the radiation source and/or the radiation detector, the radiation source and/or the radiation detecting means being moved to perform a plurality of imaging operations of the subject, and is characterized by comprising the steps of:

moving the radiation source and/or the radiation detecting means according to a predetermined pattern, performing a plurality of imaging operations of a reference subject placed at a known position, and calculating the actual amounts of movement of the radiation source and/or the radiation detecting means based on the projected position of the reference subject within each image obtained by the plurality of imaging operations;

specifying the amounts of movement of the subject within a plurality of images, which are obtained by moving the radiation source and/or the radiation detecting means according to the predetermined pattern and performing a plurality of imaging operations;

calculating estimated amounts of movement of the subject within a plurality of images which are obtained by moving the radiation source and/or the radiation detecting means according to the predetermined pattern for the actual amounts of movement and performing a plurality of imaging operations; and calculating a body movement evaluation value that indicates the degree of body movement of the subject, based on a difference between the amounts of movement of the subject and the estimated amounts of movement of the subject.

Note that the body movement measuring method of the present invention may be provided as a program that causes a computer to execute the body movement measuring method.

In the second radiation imaging apparatus, the body movement measuring method, and the body movement measuring program of the present invention, the "body movement evaluation value" is not limited to a value that indicates the actual distance that the subject has moved, and may be a normalized value or a value that indicates whether body movement has occurred, by providing a predetermined threshold value.

With respect to calculation of the actual amounts of movement of the radiation source and/or the radiation detecting means, the amount of movement of the reference subject can be specified from the projected positions (coordinates within images) of the reference subject in two images obtained at two imaging positions, and the actual amounts of movement of the radiation source and/or the radiation detecting means can be calculated based on the amount of movement of the reference subject. Alternatively, the position of the imaging system can be directly calculated from the projected position (coordinates within images) within each image obtained at each imaging position, and the actual amounts of movement of the radiation source and/or the radiation detecting means may be calculated by comparing the positions of the imaging system at each imaging position.

It is possible to image the reference subject and the subject individually. However, movement errors that occur in the radiation source and/or the radiation detecting means during actual imaging of the subject are reflected if the reference subject and the subject are imaged simultaneously. Therefore, body movements of the subject can be more accurately detected by imaging the reference subject and the subject simultaneously.

The first radiation imaging apparatus, the radiation imaging method, and the radiation imaging program of the present invention move the radiation detector, for example, along the predetermined axis of movement, irradiate radiation which has passed through the subject onto the radiation detector each time the position of the radiation detector changes due to the movement, and read out signals from the radiation detector each time that an imaging operation is performed, to obtain a plurality of images of the subject. Then, mechanical errors of the radiation detector are detected and corrected, to obtain mechanical error corrected images. Then, amounts of shift in the subject among the mechanical error corrected radiation images are detected, and the amounts of body movement during imaging operations are detected based on the amounts of shift. Because the mechanical errors are detected first, shifts due to body movement of the subject can be accurately detected.

The degree of shift due to body movement of the subject can be confirmed by displaying the amount of body movement.

Shifts of the subject among the mechanical error corrected radiation images may be corrected based on the amounts of body movement, to obtain body movement corrected radiation images. The body movement corrected radiation images can be accurately combined to obtain body movement corrected combined images. As a result, accurate diagnoses using the body movement corrected combined images are enabled.

The degree of accuracy in positional alignment can be confirmed, by the body movement corrected combined images being generated such that the degree of positional alignment can be visually confirmed at the portions of the body movement corrected images at which a plurality of the body movement corrected images overlap.

The amounts of body movement can be accurately discriminated, by further generating mechanical error corrected combined images, which are the mechanical error corrected radiation images combined with each other; and switchably displaying the body movement corrected combined images and the mechanical error corrected combined images.

An operator can take actions such as ceasing imaging, by a warning being issued in the case that the amounts of body movement exceed a predetermined threshold value. Therefore, the subject can be prevented from being unnecessarily exposed to radiation by continuing imaging operations although the degree of body movement is too large to enable images to be combined.

In addition, the subject being unnecessarily exposed to radiation can be prevented without burdening the operator, if the imaging means ceases irradiation of the radiation onto the subject when a warning is issued by the warning means.

The second radiation imaging apparatus, the body movement measuring method, and the body movement measuring program of the present invention measure the degree of body movement of a subject in a radiation imaging apparatus comprising a radiation source for emitting radiation, a radiation detecting means for detecting the radiation, and a moving means for moving the radiation source and/or the radiation detector, the radiation source and/or the radiation detecting means being moved to perform a plurality of imaging operations of the subject, by: moving the radiation source and/or the radiation detecting means according to a predetermined pattern, performing a plurality of imaging operations of a reference subject placed at a known position, and calculating the actual amounts of movement of the radiation source and/or the radiation detecting means based on the projected position of the reference subject within each image obtained by the plurality of imaging operations; specifying the amounts of movement of the subject within a plurality of images, which are obtained by moving the radiation source and/or the radiation detecting means according to the predetermined pattern and performing a plurality of imaging operations; calculating estimated amounts of movement of the subject within a plurality of images which are obtained by moving the radiation source and/or the radiation detecting means according to the predetermined pattern for the actual amounts of movement and performing a plurality of imaging operations; and calculating a body movement evaluation value that indicates the degree of body movement of the subject, based on a difference between the amounts of movement of the subject and the estimated amounts of movement of the subject. Therefore, it becomes possible to accurately detect the amounts of body movement of the subject based on the obtained images.

It is possible to image the reference subject and the subject individually. However, movement errors that occur in the radiation source and/or the radiation detecting means during actual imaging of the subject are reflected if the reference subject and the subject are imaged simultaneously. Therefore, body movements of the subject can be more accurately detected by imaging the reference subject and the subject simultaneously.

BRIEF DESCRIPTION OF THE DRAWINGS

FIG. 4 is a schematic side view that illustrates the manner in which a radiation image is obtained.

FIG. 5 is a collection of diagrams for explaining the states in which radiation images are recorded in a case that an imaging surface of a radiation detector is inclined and in a case that an imaging surface of a radiation detector is not inclined.

FIG. 24 is a collection of diagrams that illustrate examples of optical flow display.

FIG. 25 is a graph that illustrates an example of a relationship between the position o the imaging surface and mechanical errors.

BEST MODE FOR CARRYING OUT THE INVENTION

Figure 1:
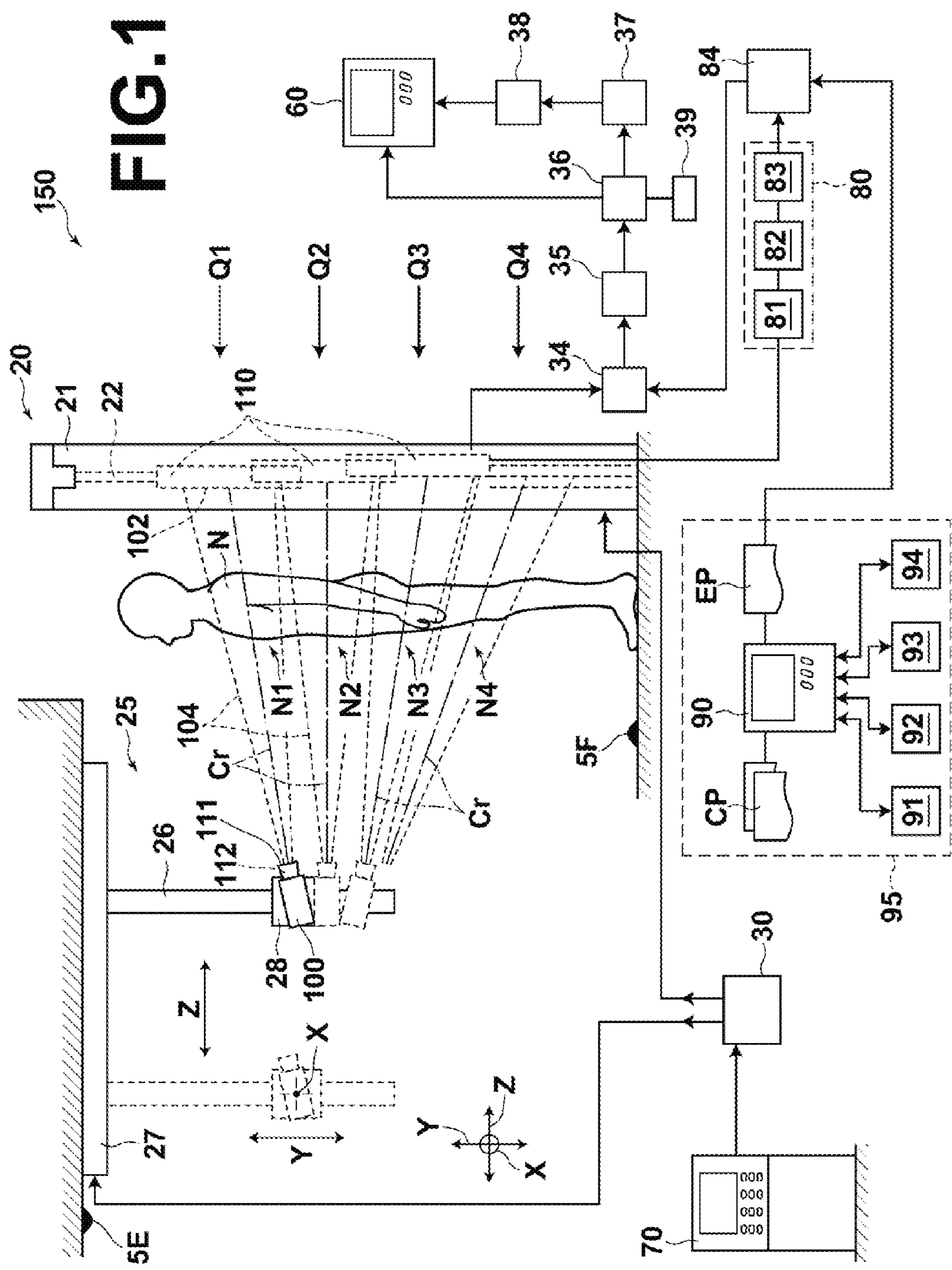
FIG. 1 is a diagram that schematically illustrates the configuration of a radiation imaging apparatus according to a first embodiment of the present invention.

Hereinafter, a first embodiment of the present invention will be described with reference to the attached drawings. FIG. 1 is a diagram that schematically illustrates the configuration of a radiation imaging apparatus according to a first embodiment of the present invention. As illustrated in FIG. 1, a radiation imaging apparatus 150 according to the first embodiment employs a single radiation source 100 and a single FPD 110 to sequentially image a plurality of adjacent regions N1, N2, . . . within a subject N. Then, a plurality of radiation images obtained thereby are combined to obtain a longitudinal radiation image that represents a large portion of the subject N.

Note that in actual longitudinal imaging systems, various mechanical errors, such as installation errors of the radiation source 100, the FPD 110, etc., and deterioration of the systems over time are possible. However, a description will be given here for a case in which only mechanical errors due to installation errors of the FPD 110 are present, to facilitate understanding.

Specifically, the radiation imaging apparatus 150 is equipped with: the radiation source 100 that emits radiation 104 through an emission window 111 onto an irradiation range determined by a collimator 112; the FPD 110, which has an imaging surface 102 (radiation detecting surface) that receives irradiation of the radiation 104 which has passed through the subject N and detects the radiation 104; a detector moving section 20 that moves the FPD 110 along the subject N; and a radiation source placing section 25 that places the radiation source 100 such that the position and orientation of the emission window 111 are in desired states. Note that in FIG. 1, the central axis of the radiation 104, of which the irradiation range is determined by the collimator 112, is denoted by Cr.

The FPD 110 detects the radiation 104 which has passed through the subject N, converts the detected radiation 104 into electrical signals, and outputs image data that represent radiation images of the subject N. Note that the FPD 110 may be of the direct conversion type that directly converts radiation to electrical charges, or may be of the indirect conversion type that temporarily converts radiation to light, and then further converts the light to electrical charges. The direct conversion type FPD is constituted by a photoconductive film formed of amorphous selenium or the like, capacitors, and TFT's (Thin Film Transistors) as switching elements. When radiation such as X rays enters the direct conversion type FPD, electron hole pairs (e-h pairs) are generated by the photoconductive film. The electron hole pairs are accumulated in the capacitors, and the electrical charges accumulated in the capacitors are read out as electrical signals via the TFT's.

In contrast, the indirect conversion type FPD is constituted by a scintillator layer, photodiodes, capacitors, and TFT's. For example, when radiation such as "CsI:Tl" enters the indirect conversion type FPD, the scintillator layer emits light (fluorescence). Light emission by the scintillator layer is photoelectrically converted by the photodiodes and accumulated in the capacitors. The electrical charges accumulated in the capacitors are read out as electrical signals via the TFTs.

The detector moving section 20 is equipped with: two support columns 21 which are erected on a floor surface 5F perpendicular thereto (to extend in the direction indicated by arrow Y in FIG. 1) that hold the FPD 110 therebetween; and a moving mechanism 22 for moving the FPD 110 in the direction indicated by arrow Y. The moving mechanism 22 may be of a known configuration, such as that in which a linear slide mechanism holds the FPD 110, which is moved by a drive source such as a motor.

When executing imaging operations to obtain radiation images to be combined, the subject N is placed along the direction in which the FPD 110 is moved. That is, imaging operations are performed with the subject N positioned to be standing on the floor.

The radiation source placing section 25 holds and moves the radiation source 100 such that the radiation source 100 faces the imaging surface 102 of the FPD 110 with the subject N therebetween. The radiation source placing section 25 is equipped with: a support column 26 that extends from the ceiling 5E in a direction perpendicular thereto; a ceiling base 27 that moves the column 26 along the ceiling 5E in the direction indicated by arrow Z in FIG. 1; and a rotatable base 28 engaged with the support column 26 so as to be movable along the direction indicated by arrow Y and rotatable about an axis perpendicular to the drawing sheet. The radiation source 100 is mounted on the rotatable base 28. Thereby the radiation source 100 is movable in the vertical direction (the direction indicated by arrow Y) and the horizontal direction (the direction indicated by arrow Z). In addition, the radiation source 100 is rotatable about an axis parallel to the X axis in FIG. 1 that passes through the approximate center of the radiation source 100. Note that the radiation source placing section 25 may also be constituted by a known linear slide mechanism and a known rotating mechanism that employ drive sources such as motors.

The radiation imaging apparatus 150 is also equipped with a longitudinal imaging control section 30 that controls the operations of the detector moving section 20 and the radiation source placing section 25. The longitudinal imaging control section 30 controls the operations of the detector moving section 20 to move the FPD 110 to positions Q1, Q2, . . . along the direction in which the subject N extends, at which radiation imaging operations are executed. At the same time, the longitudinal imaging control section 30 controls the operations of the radiation source placing section 25 to place the radiation source 100 such that the irradiation direction of the radiation 104 emitted by the radiation source 100 is oriented toward the imaging surface 102 of the FPD 110 at each of the aforementioned positions. If the radiation source 100 is driven in this state, the regions N1, N2, . . . of the subject N which are adjacent to each other are sequentially imaged, and image data that represent a plurality of partial radiation images of the subject N are obtained.

The radiation imaging apparatus 150 is further equipped with a mechanical error correcting section 34 that corrects image distortions due to mechanical errors of the imaging surface, which are included in the radiation images obtained by each of the imaging operations, based on parameters for correcting the mechanical errors of the imaging surface 102 of the FPD 110, as will be described later. In addition, the radiation imaging apparatus 150 is also equipped with: a shift detecting section 35 that detects amounts of shift within mechanical error corrected images, in which the image distortions due to mechanical errors of the imaging surface have been corrected, based on body movements of the subject N; a body movement obtaining section 36 that obtains the amounts of body movement of the subject N during imaging operations, based on the amounts of shift detected by the shift detecting section 35; and a body movement correcting section 37 that corrects the shifts of the subject within the mechanical error corrected images, based on the amounts of body movement. Further, the radiation imaging apparatus 150 is equipped with an image combining section 38 that combines the sets of image data obtained by each of the radiation imaging operations to generate a longitudinal radiation image that represents the entirety of the subject N. Here, the longitudinal radiation image generated by the image combining section 38 is displayed by an image display device 60, such as a CRT display device and a liquid crystal display device.

Note that the operation of the radiation imaging apparatus 150 as a whole is controlled by a console 70. Accordingly, information regarding the subject N, imaging conditions for obtaining the longitudinal radiation image, etc., are input to the console 70. The input information is then input to an imaging setting section (not shown) that sets the longitudinal imaging control section 30, the radiation irradiation range determined by the collimator 112, and the like. The imaging setting section sets the positions of the radiation source 100 during each radiation imaging operation, the state of the collimator 112, and the positions of the FPD 110 such that radiation images to be combined having a predetermined size are obtained by four radiation imaging operations, for example. Thereafter, the operations for obtaining the four radiation images are executed when a command is issued by the console 70.

Note that the sizes of the radiation images which are obtained by the plurality of imaging operations may be defined by setting the radiation irradiation range with the collimator 112 as described above. Alternatively, portions of the radiation images which are obtained by each imaging operation may be cut out, to adjust the lengths and widths of the images.

Next, a mechanical error detecting process performed by the radiation imaging apparatus 150 to detect mechanical errors of the imaging surface of the FPD 110 will be described. First, a case in which an automatic mechanical error detecting apparatus 80 performs this process automatically will be described. The automatic mechanical error detecting apparatus 80 is constituted by: a calibration image input section 81 that obtains image data from the FPD 110; a marker detecting section 82 to which image data is output from the calibration image input section 81; and a mechanical error detecting section 83 that receives output from the marker detecting section 82. The output of the mechanical error detecting section 83 is input to a parameter calculating section 84.

When mechanical error detection of the imaging surface is performed, imaging operations for mechanical error detection and readout operations for reading out image data that represent radiation images from the FPD 110 are independently performed separately from normal imaging of subjects, by a selection from an imaging menu input from the console 70. Here, the series of operations from the above imaging and readout to an operation for obtaining parameters for correction are referred to as calibration. In addition, radiation images obtained by the above operations are referred to as calibration images. During calibration, the FPD 110 is sequentially moved to the positions Q1, Q2, . . . and radiation 104 which has passed through markers, such as marker M1 and marker M2, is irradiated onto the FPD 110 which is stopped at each of the positions.

Figure 2:
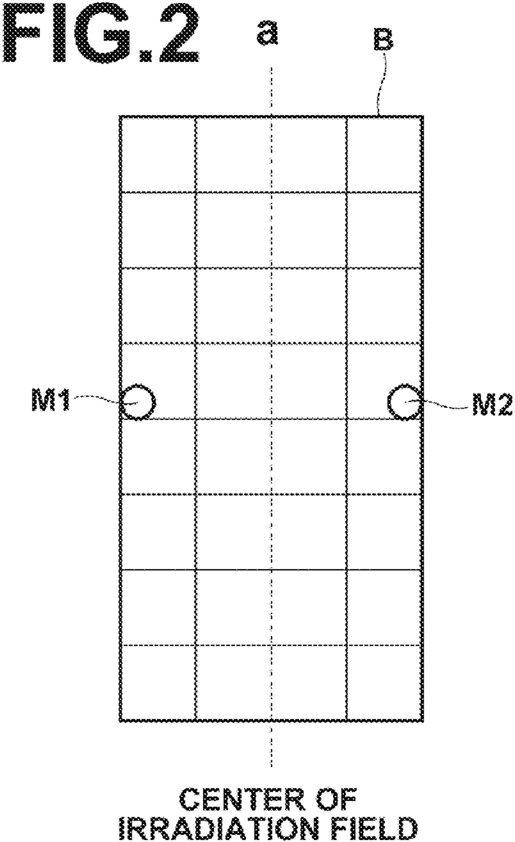
FIG. 2 is a collection of diagrams for explaining imaging of radiation images to detect inclinations of an imaging surface.
Figure 2:
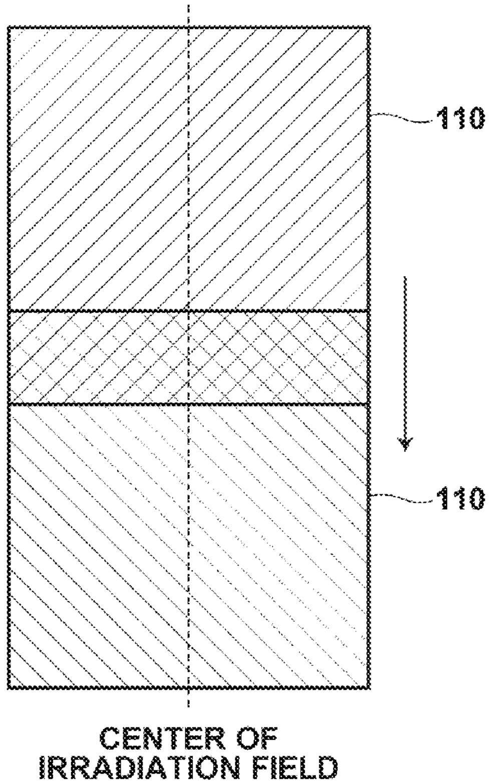

FIG. 2 is a collection of diagrams for explaining imaging operations during the calibration process. Note that FIG. 2 illustrates a case in which to imaging operations are performed during calibration, in order to simplify the explanation. In addition, a subject surface B illustrated in a of FIG. 2 is placed at the position of a subject instead of the grating 103 of FIG. 27, and the two markers M1 and M2 are placed on the subject surface B with a predetermined distance therebetween in the horizontal direction. Then, as illustrated in b of FIG. 2, the FPD 110 is moved downward from an upper position, radiation that passes through the markers M1 and M2 is irradiated onto the FPD 110 at positions prior to and following the movement, and two radiation images of the markers are obtained.

Note that in actuality, radiation imaging operations are performed such that common markers M1 and M2 are imaged within an overlapping region of the FPD 110 at the two adjacent positions Q1 and Q2. The same applies to other pairs of adjacent positions Q2 and Q3, and Q3 and Q4 a well, in the case that four imaging operations are performed. In order to perform radiation imaging operations in this manner, the markers may be arranged at appropriate intervals in the vertical direction such that the markers will be imaged regardless of the overlapping position of the FPD 110 at the two positions, or the positions Q1, Q2, . . . may be accurately determined in advance, and the markers may be placed at overlapping positions corresponding to adjacent pairs of positions.

During the two imaging operations, the FPD 110 is placed at the position indicated by the rightward rising hatching in FIG. 2B during a first imaging operation, and at the position indicated by the leftward rising hatching in FIG. 2*b* during a second imaging operation. Thereby, the markers M1 and M2 are imaged in an overlapping manner during the two imaging operations. The FPD 110 and the subject surface B are set such that the central positions thereof in the width direction match the center (in the horizontal direction) of the irradiation field of irradiation during each imaging operation. In addition, the two markers M1 and M2 are set such that they are at positions equidistant from the center of the irradiation field.

Note that it is preferable for the imaging ranges of the radiation images that include the markers, the width of overlap, the framing of each of the images, etc. to be automatically set to preset values when imaging of calibration images is selected in the imaging menu. In addition, a configuration may be adopted, in which the markers are set on a screen, a screen detection signal is generated when the screen is placed in a predetermined receiving section for imaging calibration images, and various menus for calibration imaging are displayed on a display section of the console 70 using the screen detection signal as a trigger.

As the FPD 110 is moved to each of the positions Q1, Q2, . . . and imaging operations are executed to obtain the calibration images, the FPD 110 readout operations are successively performed for each imaging operation, and image data that represent calibration images in which the markers are pictured are output from the FPD 110. The calibration image input section 81 of the automatic mechanical error detecting apparatus 80 receives the image data and transfers them to the marker detecting section 82. The marker detecting section 82 detects the positions of the markers based on image data (hereinafter, the two images represented by the image data will be referred to as "upper and lower images") successively transferred thereto from the FPD 110, which have received irradiation of radiation while being placed at two adjacent positions (Q1 and Q2, for example). Then, the marker detecting section 82 outputs information indicating the positions of the markers to the mechanical error detecting section 83. Note that known methods such as template matching may be employed to specify the positions of the markers within each image.

When the information indicating the positions of the markers is received, the mechanical error detecting section 83 detects mechanical errors of the imaging surface of the FPD 110 at two adjacent positions based on the information. Note that detection of mechanical errors using two calibration images obtained by the FPD 110 at two adjacent positions will be described below.

First, obtainment of the angle of inclination α illustrated in FIG. 27 will be described. The calibration images obtained by the aforementioned two imaging operations are those as illustrated in a of FIG. 3. The upper calibration image is that which is obtained by a first imaging operation, and the lower calibration image is that which is obtained by a second imaging operation. The markers M1 and M2 are recorded in both of the calibration images. However, if the imaging surface 102 is inclined at an angle α with respect to the surface of the panel, there will be a shift between the images of the markers M1 and M2 in the two calibration images. In contrast, if the imaging surface 102 is not inclined at an angle α with respect to the surface of the panel, the calibration images will be those as illustrated in b of FIG. 3. Therefore, the angle α can be obtained from the relationship between a of FIG. 3 and b of FIG. 3.

Figure 27:
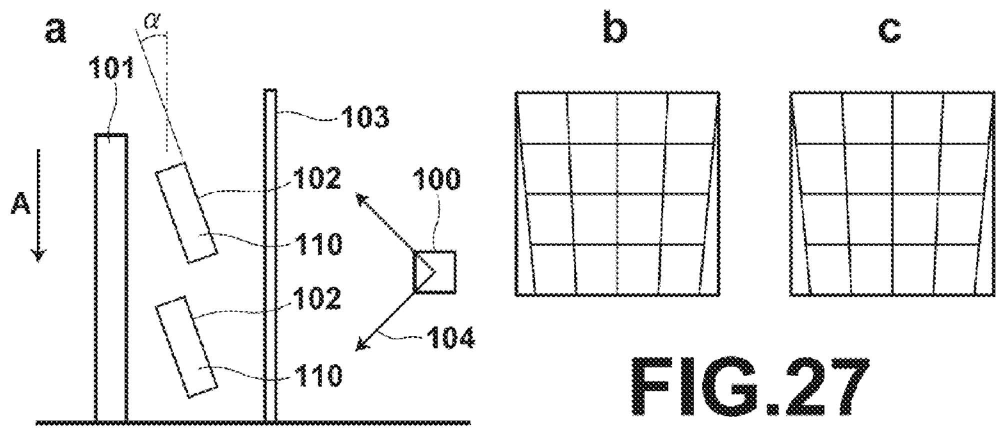
FIG. 27 is a collection of diagrams for explaining a problem encountered by conventional technology.

The angle α is an angle within a plane that includes the radiation irradiation axes of the plurality of imaging operations, that is, within a plane parallel to the drawing sheet of FIG. 27. In the present embodiment, the panel shaped FPD 110 is provided such that the surface thereof is parallel to the axis of movement that the detector moves along. Therefore, the angle α is an angle with respect to the axis of movement that the detector moves along.

Figure 3:
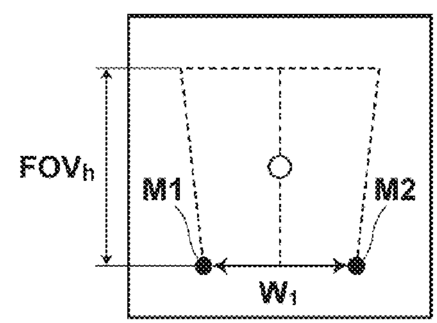
FIG. 3 is a collection of diagrams for explaining the states in which radiation images are recorded in a case that an imaging surface of a radiation detector is inclined and in a case that an imaging surface of a radiation detector is not inclined.

Here, the distance between the markers M1 and M2 is designated as $W_1$ in the first image which is obtained, and $W_2$ in the second image which is obtained. In addition, the distance along the radiation irradiating direction from the center of the imaging surface to the markers M1 and M2 is designated as d, and the distance from the radiation source 100 to the center of the imaging surface is designated as SID, as illustrated in FIG. 4. Further, twice the distance from the center of the imaging surface 102 to the midpoint between the markers M1 and M2 is designated as $FOV_h$, as illustrated in FIG. 3 and FIG. 4. The relationships among each of the distances above are represented by Formula (1) below, from which Formula (2) is derived.

$$\begin{cases} W_1 \times \frac{SID + d}{SID} = W_2 \times \frac{SID - d}{SID} \\ \sin\alpha = \frac{2d}{FOV_h} \end{cases} \quad \text{Formula (1)}$$

$$\sin\alpha = \frac{2(W_2 - W_1) \cdot SID}{FOV_h \cdot (W_1 + W_2)} \quad \text{Formula (2)}$$

The angle of inclination α of the imaging surface 102 can be obtained from each of the aforementioned distances, based on Formula (2). Strictly speaking, the angle α which is obtained varies because the difference between $W_1$ and $W_2$ will vary according to the relationship between the height positions of the FPD 110 and the radiation source 100. However, d is generally sufficiently smaller than SID, and therefore the above variance can be ignored, and the angle α can be approximated by Formula (2).

Next obtainment of the angle of inclination γ illustrated in FIG. 28 will be described. Note that the angle of inclination γ is an angle of the imaging surface within the plane of the imaging surface 102 with respect to the axis of movement that the detector moves along.

The calibration images obtained by the two imaging operations are those illustrated in a of FIG. 5. In a of FIG. 5, the upper calibration image is that which is obtained by the first imaging operation, and the lower calibration image is that which is obtained by the second imaging operation. The markers M1 and M2 are recorded in both of the calibration images. However, if the two dimensional matrix of the pixel sections G is inclined at an angle γ with respect to an edge of the panel as illustrated in FIG. 28, there will be a shift between the images of the markers M1 and M2 in the two calibration images. In contrast, if the two dimensional matrix is not inclined at an angle γ with respect to the edge of the panel, the calibration images will be those as illustrated in b of FIG. 5. Therefore, the angle γ can be obtained from the relationship between a of FIG. 5 and b of FIG. 5.

That is, square gratings having a line segment that connects the centers of the images of the markers M1 and M2 as an edge thereof are set, as illustrated by the broken lines in FIG. 5. By moving one of the radiation images in the vertical and horizontal directions such that the centers of the gratings are matched, the angle γ can be obtained based on the amounts of movement.

Figure 6:
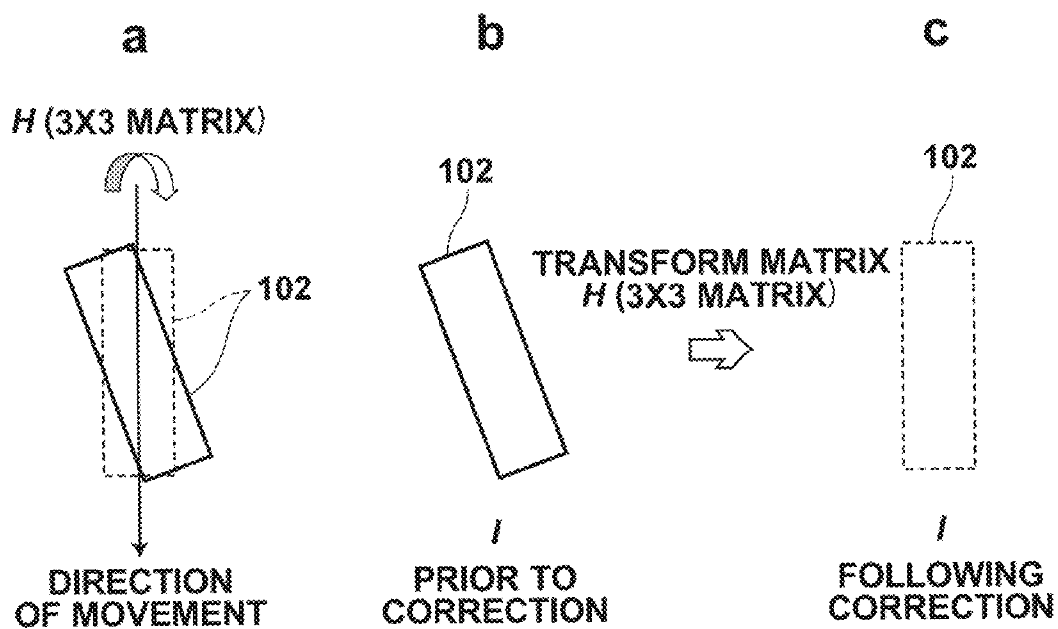
FIG. 6 is a collection of diagrams for schematically explaining an example of an image correcting method according to the present invention.

Next, a process for correcting distortions in radiation images caused by the inclinations based on the angles α and γ obtained in the above manners will be described. As an example, a case in which the imaging surface 102 is inclined at an angle of α as indicated by the solid lines in a of FIG. 6 and a first imaging operation and a second imaging operation are performed in the state illustrated in b of FIG. 6 will be considered. In this case, if the radiation image of the subject which is read out later is corrected to become a radiation image obtained in the state illustrated in c of FIG. 6, distortion due to the angle α can be eliminated. Therefore, shifts will not be present at the boundaries when the two radiation images are combined. Note that in the present embodiment, correction is also performed such that distortion in the image due to inclination of the imaging surface 102 at the angle γ is eliminated.

Here, it is assumed that the movement of the FPD 110 is reproducible. When images of a subject are obtained, the FPD 110 is moved in the same manner as that when the angles α and γ are obtained.

Figure 7:
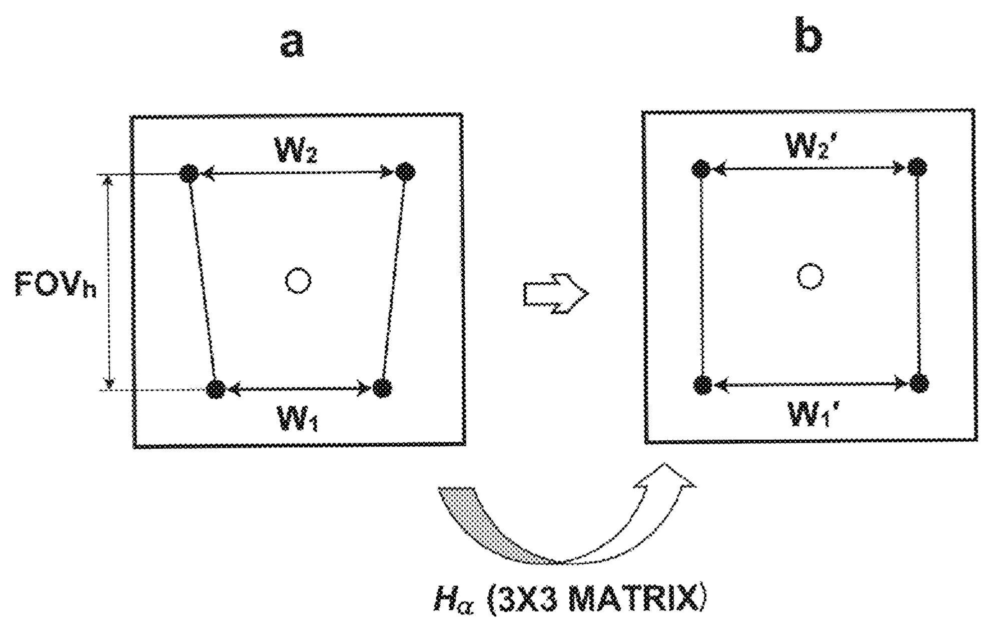
FIG. 7 is a collection of diagrams for schematically explaining another example of an image correcting method according to the present invention.

Next, obtainment of parameters to be employed in the process for correcting mechanical error will be described. Here, a method by which a transformation matrix is obtained from the obtained angles α and γ will be described. More specifically, a method in which four or more corresponding points are set, and a transformation matrix is obtained from the correspondence of the four or more points prior to and following transform will be described. First in order to correct distortion of an image due to inclination of the imaging surface in the direction of the angle α, parameters that enable correction such that the four corresponding points (that would form a square if recorded correctly) indicated by black circles in a of FIG. 7 are corrected to those illustrated in b of FIG. 7 are obtained. Here, if the lengths of the lower edge and the upper edge of the distorted square prior to correction are respectively designated as $W_1$ and $W_2$, and the lengths of the lower edge and the upper edge following correction are designated as $W_{1'}$ and $W_{2'}$, the relationships of Formula (3) and Formula (4) below will be established. Note that the definitions of the variables other than $W_1$, $W_2$, $W_{1'}$, and $W_{2'}$ are the same as those described previously.

$$W_1' = W_1 \times \frac{SID + d}{SID} \quad \text{Formula (3)}$$

$$\sin\alpha = \frac{2d}{FOV_h}$$

$$W_2' = W_2 \times \frac{SID - d}{SID} \quad \text{Formula (4)}$$

$$\sin\alpha = \frac{2d}{FOV_h}$$

The relationship of Formula (5) below can be derived from Formula (3), and the relationship of Formula (6) below can be derived from Formula (4).

$$W_1' = W_1 \times \left(1 + \frac{FOV_h \cdot \sin\alpha}{2SID}\right) \quad \text{Formula (5)}$$

-continued $$W_2' = W_2 \times \left(1 - \frac{FOV_h \cdot \sin\alpha}{2SID}\right) \quad \text{Formula (6)}$$

Figure 8:
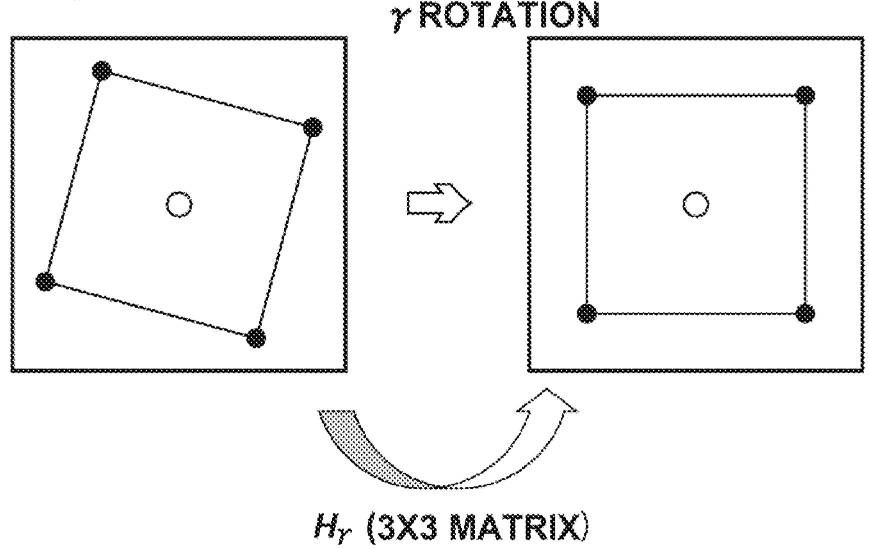
FIG. 8 is a collection of diagrams for schematically explaining still another example of an image correcting method according to the present invention.

Then, the values within the parentheses at the right sides of Formula (5) and Formula (6) are obtained from the known values of SID and $FOV_h$, and these values are respectively designated as a parameter for transforming $W_1$ to $W_1'$, and a parameter for transforming $W_2$ to $W_2'$. Then, a (3×3) matrix $H_\alpha$ that transforms image data that represents a two dimensional radiation image from that illustrated in a of FIG. 7 to that illustrated in b of FIG. 7 is obtained from these parameters.

a of FIG. 8 and b of FIG. 8 respectively illustrate the relationship between radiation images prior to and following rotation by the aforementioned angle γ. A (3×3) matrix $H_\gamma$ that transforms image data that represents a two dimensional radiation image from that illustrated in a of FIG. 8 to that illustrated in b of FIG. 8 is obtained. Note that the matrix for transforming an image by rotation may be obtained by a conventionally known method.

The inclinations of the imaging surface 102 related to the directions of the angles α and γ described above are sums of linear phenomena. Therefore, the matrices can be linked by the multiplication formulas of Formula (9) below.

$$H=H_\alpha H_\gamma \text{ or } H=H_\gamma H_\alpha \quad \text{Formula (9)}$$

If the image data that represent a radiation image of the subject obtained by the first imaging operation is transformed using the matrix H following the multiplication of Formula (9) as a transform matrix, the transformed image data will be that in which distortions of the image due to the inclinations of the imaging surface 102 in the directions of the angles α and γ are both corrected. This applies in the case that the transformation is performed on the image data that represents a radiation image of the subject obtained by the second imaging operation as well. By performing this transform, the mechanical errors of the two radiation images can be corrected. Accordingly, when the two mechanical error corrected radiation images are combined, shifts being generated at the boundaries can be prevented within a combined image (a longitudinal radiation image).

Figure 9:
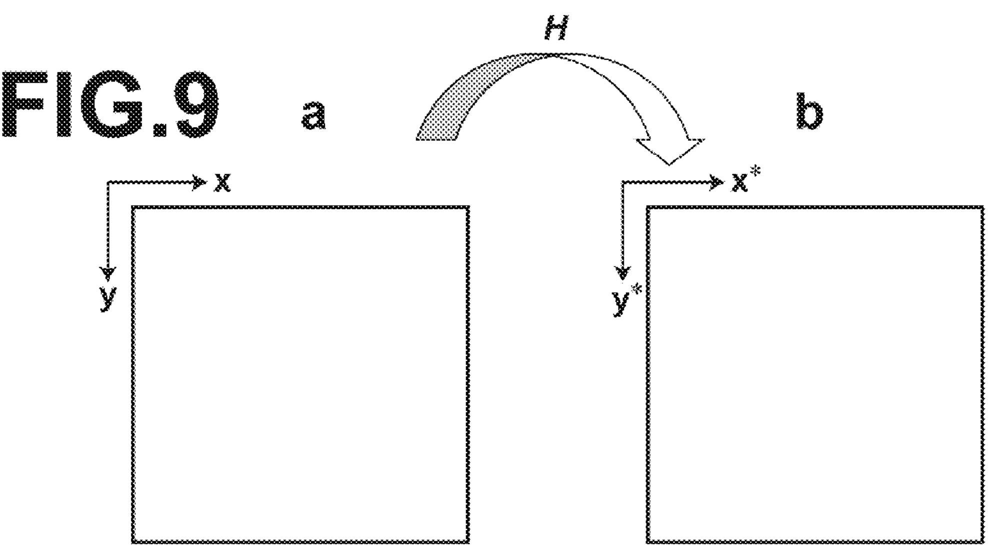
FIG. 9 is a collection of diagrams that illustrate coordinate systems of an image prior to and following image correction.

Two dimensional projection transform will be described as a specific example of an image transform process that employs the transform matrix described above. As illustrated in a of FIG. 9 and b of FIG. 9, the coordinate system prior to the two dimensional projection transform process being administered is set as an xy coordinate system, and the coordinate system following the two dimensional projection transform process being administered is set as an x*y* coordinate system. The two dimensional projection transform is commonly represented by Formula (12) below in a homogenous coordinate system.

$$(x \;\; y \;\; 1)\begin{pmatrix} a & b & p \\ c & d & q \\ t_x & t_y & s \end{pmatrix} = (X^* \;\; Y^* \;\; w^*) \quad \text{Formula (12)}$$

wherein $X^* = w^* x^*$, $Y^* = w^* y^*$ $$H = \begin{pmatrix} a & b & p \\ c & d & q \\ t_x & t_y & s \end{pmatrix}$$

Note that a homogenous coordinate system is that in which an n dimensional problem is processed as an (n+1) dimensional problem to simplify and generalize calculations. The transform matrix H has nine elements but eight degrees of freedom, and may be obtained if at least four points correspond to each other (that is two xy coordinates can be obtained for each corresponding point).

After the transform matrix H is obtained as described above, the original image data is designated as I, and corrected image data I' can be obtained as I'=HI.

Note that in the embodiment described above, image data are corrected based on the obtained angles of inclination α and γ of the imaging surface, to eliminate distortions in images caused by these inclinations. Alternatively, it is possible to not execute such correction, but to manually correct the mounting position of the imaging surface 102 such that the angles of inclination α and γ are eliminated. It is also possible for the correction of the mounting position of the imaging surface 102 to be performed automatically based on the angles of inclination α and γ with an imaging surface position correcting means incorporated into the FPD 110.

The aforementioned grating may be employed instead of the markers M1 and M2 that indicate two points as the markers to be employed by the present embodiment.

Next, correction of distortions in images due to the angles of inclination α and γ and displacements Δy and Δx respectively illustrated in FIG. 30 and FIG. 31 will be described. Note that in the following description, the angle of inclination α may be referred to as "pitching angle" and the FPD 110 may be referred to simply as "panel", in order to clarify and simplify the description. The method for correcting distortions in images represents positions within images obtained by a panel having inclinations and displacements with an xy coordinate system, represents positions within ultimate corrected images with an x"y" coordinate system, and obtains what (x", y") positions image data at (x, y) positions are related to.

Figure 10:
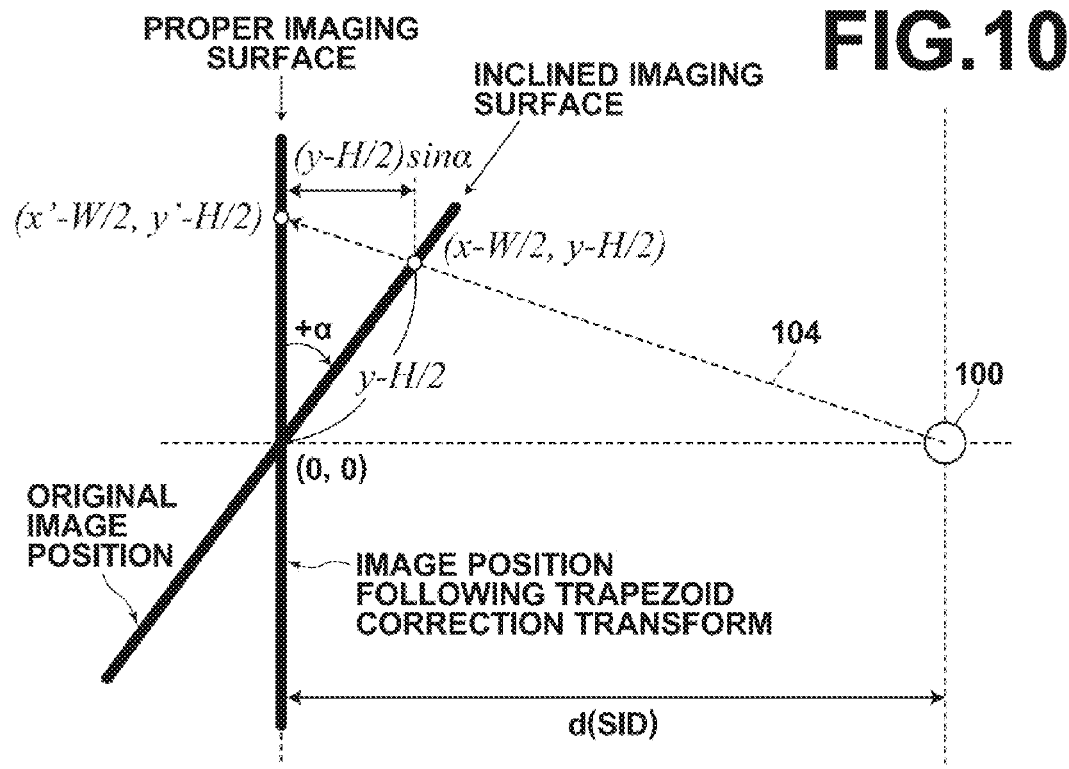
FIG. 10 is a diagram for schematically explaining an example of an image correcting method according to the present invention.

First, a case in which trapezoidal distortion of an obtained image as illustrated in FIG. 27 due to the panel being inclined at a pitching angle α as illustrated in FIG. 10 is corrected will be described. Note that this correction will be referred to as "trapezoid correction" hereinafter. Here, the imaging surface is not inclined within the panel, but the pitching angle α of the panel becomes the pitching angle α of the imaging surface, that is, the pixel sections of the imaging surface. In addition, the "PROPER IMAGING SURFACE" in FIG. 10 denotes an imaging surface that does not have a pitching angle α. The trapezoid correction obtains what (x', y') positions image data at (x, y) positions are related to if positions on the proper imaging surface are represented by an x' y' coordinate system.

Here,

α: pitching angle (−90°<α<+90°)

x, y: coordinates on an inclined panel (actual image data)

x',y': coordinates on an image following trapezoid correction transform d: SID (Source Image Distance; the distance between the panel and the radiation source)

W: image width

H: image height

From FIG. 10, the enlargement/reduction ratio of the image in the x direction due to the pitching angle α being present is represented as follows.

$$d:d-y\sin\alpha=x':x \quad \text{Formula (19)}$$

If the origin of the coordinate system is moved from a position on the inclined imaging surface at which a normal line that passes through the center of the radiation source 100 lands to a position on the proper imaging surface at which a normal line that passes through the center of the radiation source 100 lands, that is, the position indicated by (0, 0) in FIG. 10, Formula (20) below is established from Formula (19) above.

$$d:d-(y-H/2)\sin\alpha = x'-W/2:x-W/2 \qquad \text{Formula (20)}$$

Accordingly, the relationship between positions (x, y) and positions (x', y') is represented by Formulae (21) below.

$$x' = \frac{d}{d-(y-H/2)\sin\alpha}(x-W/2)+W/2 \qquad \text{Formula (21)}$$
$$y' = y$$

Strictly speaking, enlargement and reduction also occur in the y direction. However, the enlargement and reduction in the y direction is sufficiently small such that y' can be approximated as y.

Figure 28:
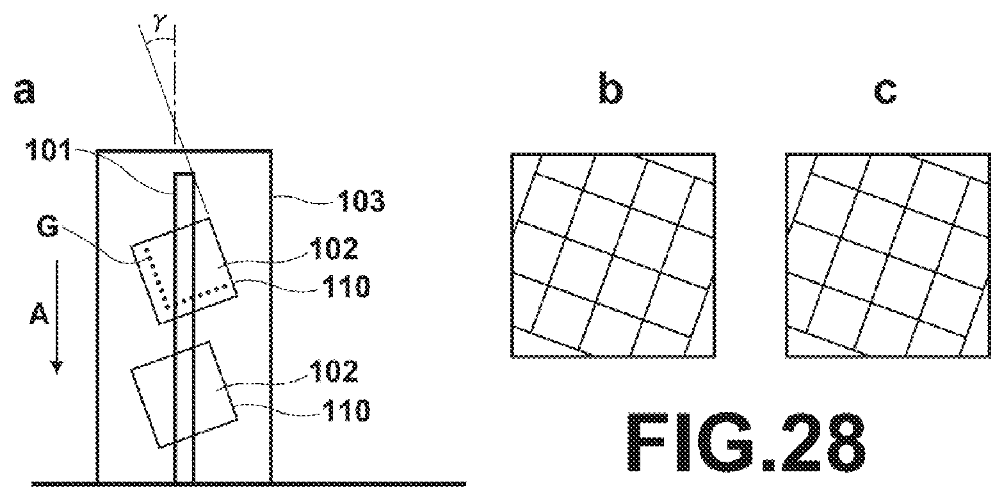
FIG. 28 is a collection of diagrams for explaining another problem encountered by conventional technology.
Figure 29:
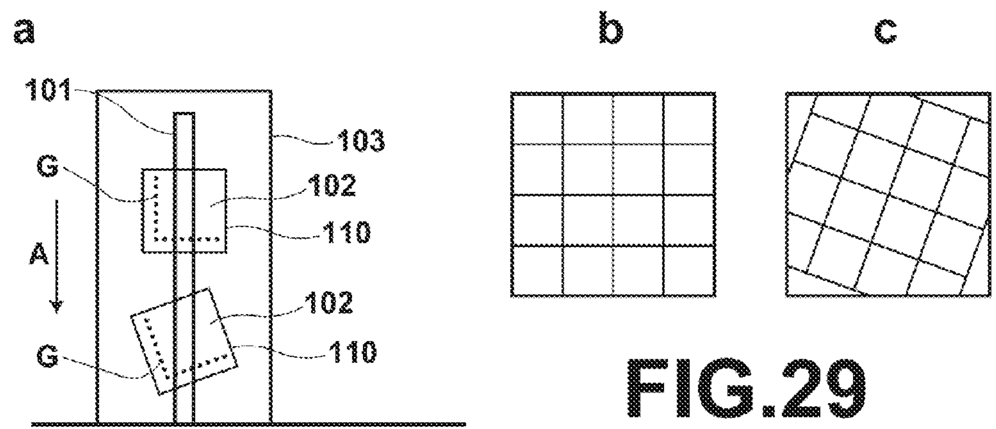
FIG. 29 is a collection of diagrams for explaining still another problem encountered by conventional technology.
Figure 30:
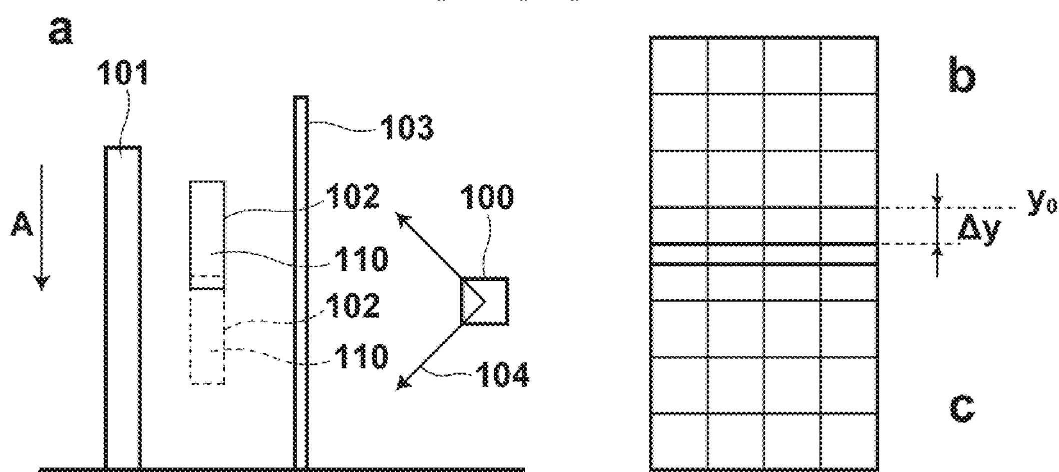
FIG. 30 is a collection of diagrams for explaining still yet another problem encountered by conventional technology.
Figure 31:
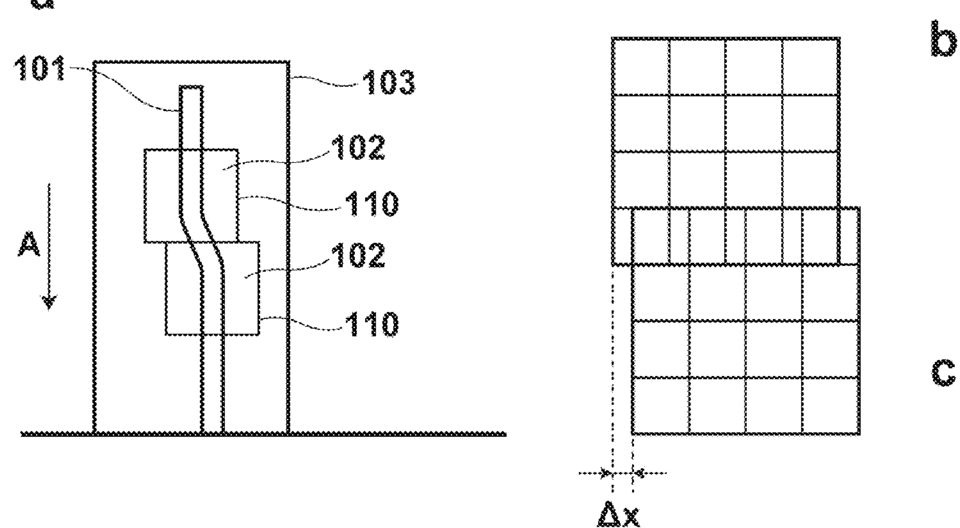
FIG. 31 is a collection of diagrams for explaining another problem encountered by conventional technology.

Next, correcting distortions of images caused by the angle of inclination γ illustrated in FIG. 28 and the displacements Δy and Δx respectively illustrated in FIG. 30 and FIG. 31 will be considered. Here, the displacement Δx is represented as $t_x$, and the displacement Δy is represented as $t_y$. The conditions are as shown below.

(x,y): original image coordinates (x',y'): coordinates after trapezoid correction transform (x",y"): ultimately corrected image coordinates $t_x$: amount of movement in the x direction $t_y$: amount of movement in the y direction γ: angle of rotation in the xy plane The relationship between positions (x, y) prior to trapezoid correction transform and positions (x', y') following trapezoid correction transform is as shown in Formulae (21). If positions within the ultimately corrected image are represented by an x"y" coordinate system, the relationship between positions (x", y") in the x"y" coordinate system and positions (x', y') after trapezoid correction transform is as shown below.

$$\begin{pmatrix} x'' \\ y'' \\ 1 \end{pmatrix} = \begin{pmatrix} 1 & 0 & t_x \\ 0 & 1 & t_y \\ 0 & 0 & 1 \end{pmatrix} \begin{pmatrix} \cos\gamma & \sin\gamma & 0 \\ -\sin\gamma & \cos\gamma & 0 \\ 0 & 0 & 1 \end{pmatrix} \begin{pmatrix} x' \\ y' \\ 1 \end{pmatrix} \qquad \text{Formula (23)}$$

As described above, image data at positions (x, y) are converted to image data at positions (x", y") by performing the two transforms of Formulae (21) and Formula (23). If original image data related to positions (x, y), obtained by performing readout operations from the FPD 110 during each of the radiation irradiation operations, are corrected to become image data related to positions (x", y") by the two transforms described above, the occurrence of shifts at boundaries can be prevented when the corrected image data are combined to form a single longitudinal image.

The mechanical error detecting section 83 obtains the angles of inclination α and γ and the displacements Δy and Δx as described above, then inputs the information that represents these mechanical errors to the parameter calculating section 84. When this information is received, the parameter calculating section 84 calculates parameters for performing image transform from the angles of inclination α and γ and the displacements Δy and Δx, and inputs the parameters to the mechanical error correcting section 34.

Normal radiation imaging operations, that is, operations to sequentially obtain radiation images of the plurality of adjacent regions N1, N2, . . . of the subject N to be combined into a longitudinal image, are basically performed after the aforementioned calibration is performed. Alternatively, normal radiation imaging operations may be performed on a daily basis, and calibration may be performed as appropriate during the normal radiation imaging operations. Image data which are successively output from the FPD 110 which is placed at two adjacent positions (Q1 and Q2, for example) and receives irradiation of radiation during normal radiation imaging operations are transferred to the image combining section 38 and provided for image combination. Correction to eliminate distortions in the images is performed by the mechanical error correcting section 34 based on the aforementioned parameters prior to the images being combined. Note that the mechanical error correcting section 34 is equipped with a memory section (not shown) for storing the parameters.

The correcting process is a two dimensional projection transform process as described above. Accordingly, the parameters are values of the (3×3) transform matrices of the two dimensional projection transform. The image data on which the correction has been administered are those in which mechanical errors of the imaging surface 102 have been corrected.

Note that it is possible to employ shear coefficients as the parameters instead of those exemplified above, to eliminate the distortions in the images with increased accuracy. That is, it is known that shear transform occurs in two dimensional projection transform according to the ratios among a, b, c, and d, which are coefficients of the aforementioned (3×3) transform matrices. The coefficients a, b, c, and d are referred to as shear coefficients. By performing two dimensional projection transform employing the shear coefficients expecting shear transform to occur, distortions of images due to mechanical errors can be more positively eliminated. Note that shear transform and shear coefficients are described in detail in F. Yamaguchi, "Geographic Processing Engineering", Nikkan Kogyo Shimbun Press, pp. 73-75, 1981.

Figure 11:
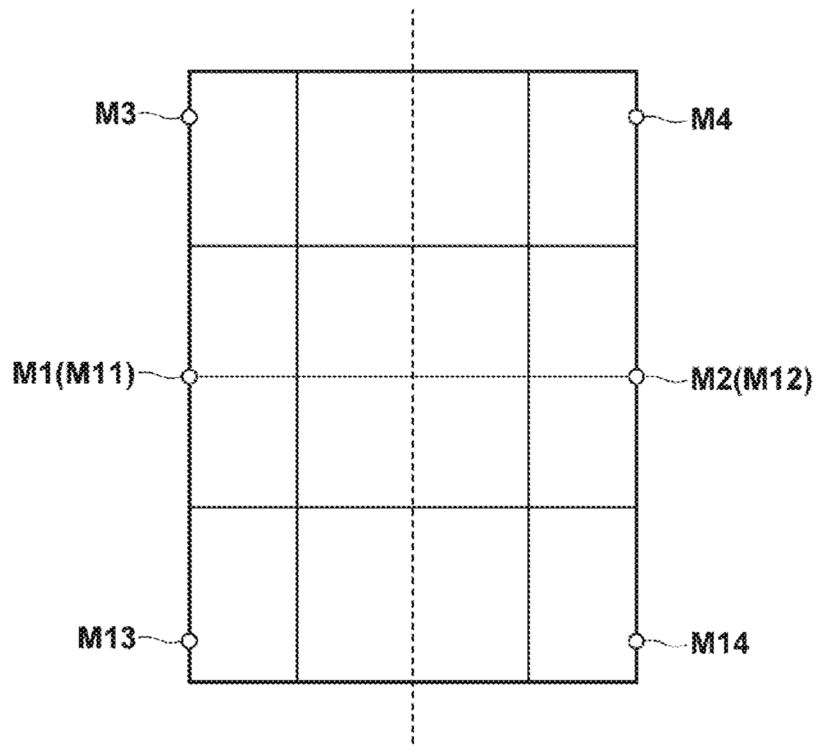
FIG. 11 is a diagram for explaining an example of parameter calculations.
Figure 12:
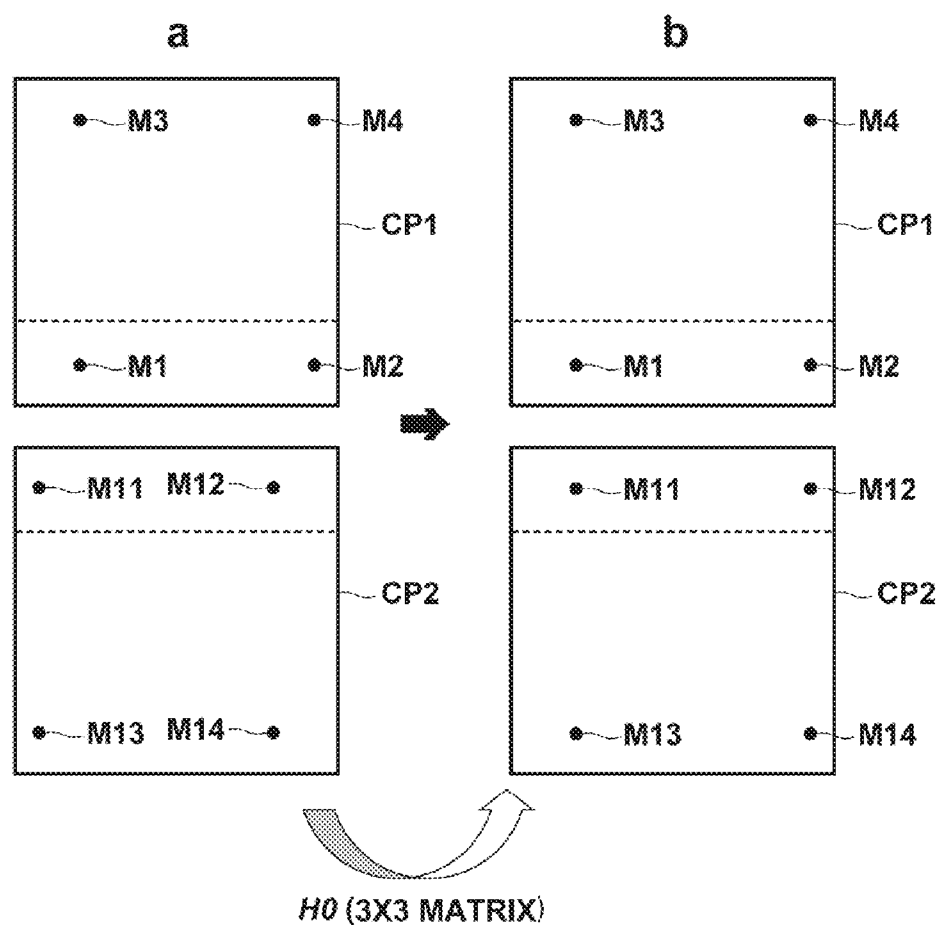
FIG. 12 is a collection of diagrams for explaining another example of parameter calculations.

Note that the method by which the parameters are calculated is not limited to the technique described above. For example, six markers M1 (M11), M2 (M12), M3, M4, M13, and M14 may be placed on the subject surface B as illustrated in FIG. 11 when calculating parameters for correcting two vertically arranged radiation images, to calculate the parameters. In this case, the FPD 110 is moved and imaging operations are performed such that the markers M1 (M11) and M2 (M12) overlap. FIG. 12 is a collection of diagrams that illustrate two calibration images obtained by calibration imaging. As illustrated in a of FIG. 12, one calibration image CP1 includes four markers M1 through M4, and the other calibration image CP2 includes four markers M11 through M14. Note that the marker M1 and the marker M11 are the same marker, as well as the marker M2 and the marker M12. However, the images included in the calibration image CP1 are denoted as M1 and M2, and the images included in the calibration image CP2 are denoted as M11 and M12 to simplify the description.

Transform parameters are calculated for the calibration image CP2, and a 3×3 transform matrix H0 that corrects relative shifts between the calibration images C1 and C2 is calculated. In this case, points prior to transform and points following transform are designated as corresponding points.

A transform matrix that matches the positions of the markers M1 and M2 included in the calibration image CP1 and the positions of the markers M11 and M12 included in the calibration image CP2 is obtained from four or more corresponding points. By performing imaging operations such that the four markers N1 through M4 and the four markers M11 through M14 are respectively included in the calibration images CP1 and CP2 as illustrated in FIG. 11, there will be four corresponding points, and therefore the transform matrix H0 can be calculated. The calibration image CP2 can be transformed such that the positions of the markers M1 and M2 included in the calibration image CP1 match the positions of the markers M11 and M12 included in the calibration image CP2 illustrated in b of FIG. 12, by employing the transform matrix H0.

Figure 13:
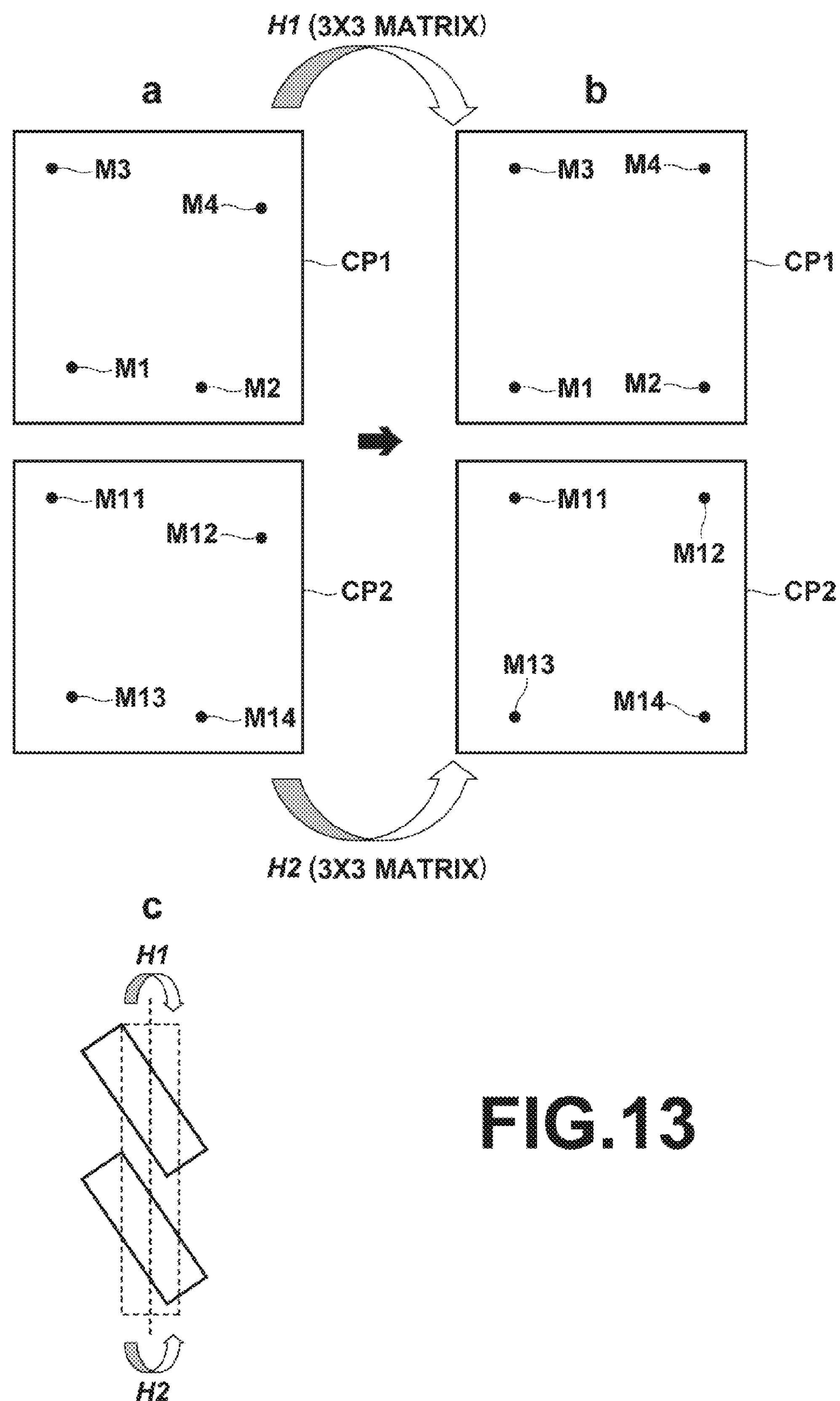
FIG. 13 is a collection of diagrams for explaining still another example of parameter calculations.

Alternatively, transform parameters may be calculated for both calibration images CP1 and CP2 such that the shape in which markers M1 through M4 are arranged within the calibration image CP1 and the shape in which markers M11 through M14 are arranged within the calibration image CP2 as illustrated in a of FIG. 13 match, as illustrated in b of FIG. 13, and such that the positions of the markers M1 and M2 included in the calibration image CP1 match the positions of the markers M11 and M12 included in the calibration image CP2. Transform matrices H1 and H2 (refer to c of FIG. 13) that correct the parallelism between the subject surface and the imaging surface 102 may be calculated from the transform parameters. In this case as well, by performing imaging operations such that the four markers M1 through M4 and the four markers M11 through M14 are respectively included in the calibration images CP1 and CP2 as illustrated in FIG. 11, there will be four corresponding points, and therefore the transform matrices H1 and H2 can be calculated.

The calibration images CP1 and CP2 can be transformed such that the shape in which markers M1 through M4 are arranged within the calibration image CP1 and the shape in which markers M11 through M14 are arranged within the calibration image CP2 match, by employing the transform matrices H1 and H2.

Figure 14:
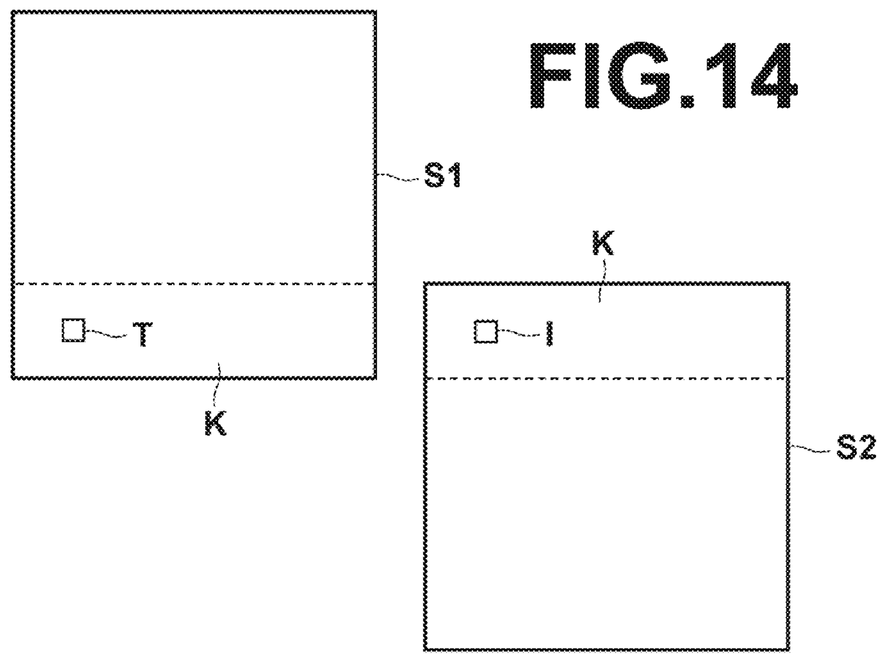
FIG. 14 is a diagram for explaining template matching.

Next, detection by the shift detection section 35 of amounts of shift based on body movements of the subject N will be described. Mechanical errors within the radiation images which have undergone mechanical error correction by the mechanical error correcting section 34 are corrected. Therefore, shifts of the subject included in these radiation images represent body movements of the subject during imaging operations. The shift detecting section 35 employs adjacent mechanical error corrected radiation images (hereinafter, also referred to as "radiation images") to detect the amounts of movement when the images within overlapping regions among the radiation images are matched most closely. FIG. 14 is a diagram for explaining detection of body movement of a subject, based on an image within an overlapping region K between two radiation images.

As illustrated in FIG. 14, the amount of movement that appears due to body movements of the subject N of an image within the overlapping region K between two radiation images S1 and S2 is detected by template matching, which searches for the portion within an image (the overlapping region of the radiation image S2) at which the same features within another image (a template T present within the overlapping region of the radiation image S1) is present.

Specifically, the correlative values between the template T and search target images I, which are the same size as the template T and searched within the overlapping region K of the radiation image S2, are calculated. The amount of pixel shift (amount of movement) of the template T between a reference position of the template T (a position at which correlation becomes greatest in the case that there is no body movement) and a position of the search target I when the correlative value is greatest is detected as an amount of shift based on body movement.

Note that in the present embodiment, markers may be imparted to the subject surface B during imaging operations. In this case, images of markers are included in the radiation images S1 and S2. In this case, the markers are imparted to predetermined ranges of the subject surface B. Therefore, it is preferable for the markers to be detected at corresponding ranges of the radiation images S1 and S2, and for templates to be provided at regions of the overlapping region K other than regions at which the markers are included, to perform template matching.

Figure 15:
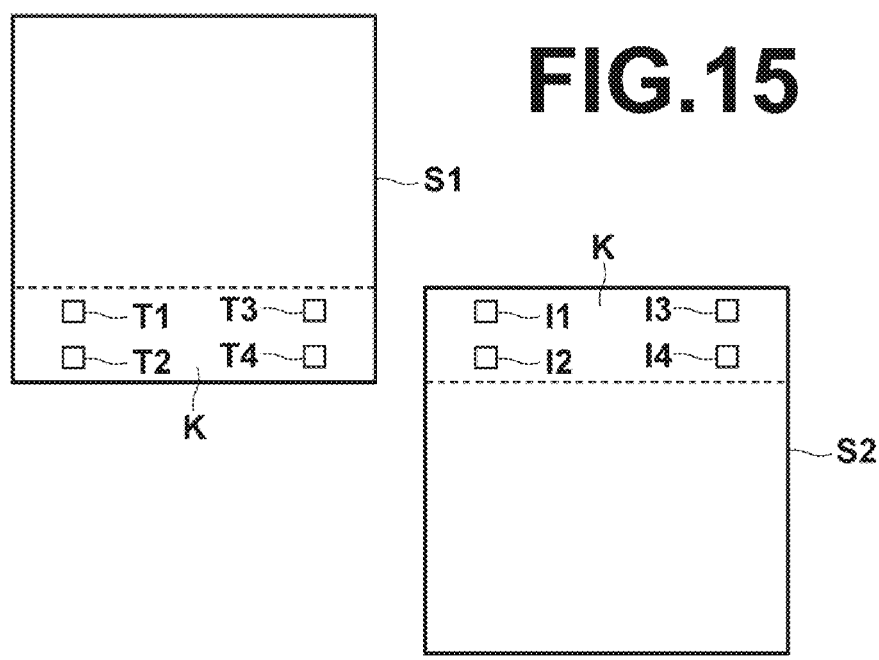
FIG. 15 is a diagram for explaining template matching.

Alternatively, template matching may be performed employing a plurality (four in the case of FIG. 15) of templates T1 through T4 as illustrated in FIG. 15, to detect a plurality of amounts of shift. In addition, template matching may be performed using templates having sizes that differ in a stepwise manner.

Next, the obtainment of the amount of body movement by the body movement obtaining section 36 will be described. The body movement obtaining section 36 obtains the amount of body movement of the subject N based on the amounts of shift detected by the shift detecting section 35. Here, in the case that the shift detecting section 35 detects the amount of shift employing only a single template, the body movement obtaining section 36 employs the amount of shift detected by the shift detecting section 35 as the amount of body movement as is. In the case that the shift detecting section 35 detects a plurality of amounts of shift as amounts of shift, the body movement obtaining section 36 employs each of the plurality of amounts of shift as an amount of body movement. Note that the amount of shift having the greatest correlative value when the template matching described above is performed may be obtained as the amount of body movement. Alternatively, an average value of a plurality of amounts of shift may be obtained as the amount of body movement. As a further alternative, each of a plurality of amounts of shift may be weighted according to the correlative value when the amount of shift is calculated, then a weighted average of the amounts of shift may be obtained as a single amount of body movement.

In the above description, the amount of body movement is obtained using corrected images, in which mechanical errors have been corrected, as input images. Alternatively, the amounts of shift within overlapping regions may be obtained from within original images prior to the mechanical errors being removed by the techniques described above, amounts of movement that include both mechanical errors and body movements may be determined from the amounts of shift, and amounts of movement, which are the those obtained by subtracting known mechanical errors from the determined amounts of movement or by dividing the determined amounts of movement by the known mechanical errors, may be obtained as the amounts of movement.

When inputting original images to obtain amounts of shift as described above, known mechanical errors may be applied to the overlapping region. That is, images in which mechanical errors have been corrected only for overlapping regions of two adjacent images may be produced, or the amount of body movement may be obtained from the results of subtraction of known mechanical errors from amounts of shift obtained by template matching or the results of division of amounts of shift obtained by template matching by the known mechanical errors.

Note that in the present embodiment, calibration using markers is performed without the subject is performed in advance to obtain mechanical errors. Alternatively, markers may be provided such that the markers are pictured within the overlapping portions of adjacent images and imaging operations may be performed, to perform calibration and calculation of amounts of body movement each time that imaging operations of the subject is executed. Thereby, amounts of body movement can be detected during each imaging operation with high accuracy, and the amounts of body movement can be detected while taking the deterioration of the main moving components of the imaging apparatus over time into consideration.

Figure 16:
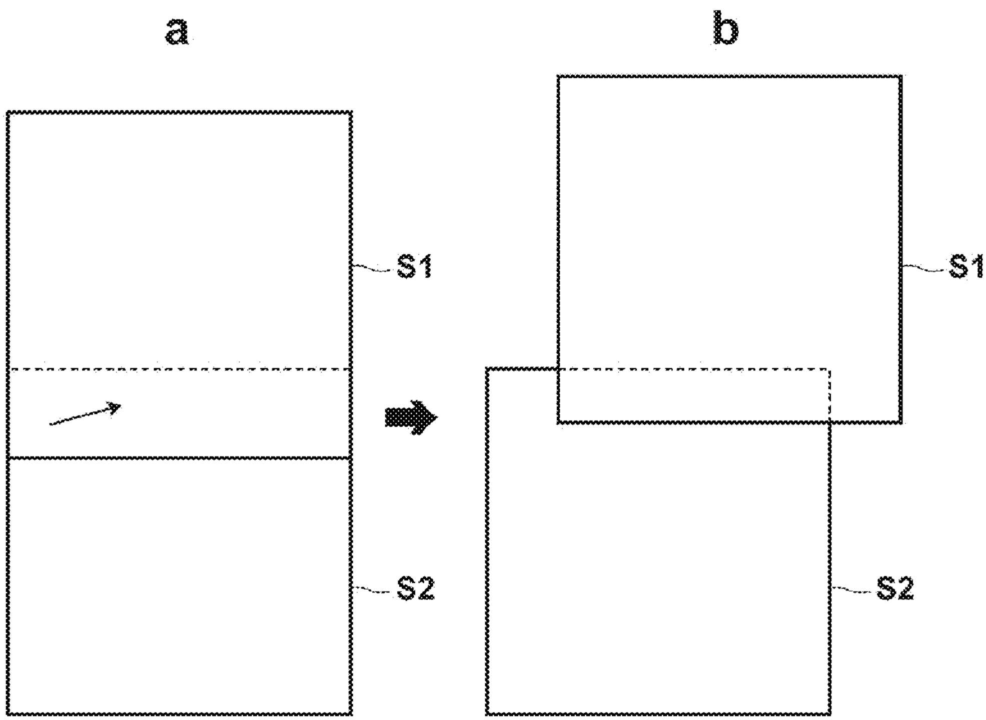
FIG. 16 is a collection of diagrams for explaining body movement correction.

The body movement correcting section 37 administers correction to eliminate distortions in images caused by body movements of the subject N on the radiation images in which mechanical errors have been corrected, based on the amounts of body movement obtained by the body amount obtaining section 36. Here, a case in which distortions in two radiation images are corrected will be described. In the case that an amount of body movement is detected as a single value as illustrated in a of FIG. 16, body movement correction is performed by relatively shifting the two radiation images S1 and S2 based on the amount and the direction of body movement, as illustrated in b of FIG. 16. In the case that a plurality of amounts of body movement are detected, body movement correction is performed by relatively warping the plurality of radiation images such that the position of the template employed to detect amounts of shift and the position of the search target image match.

The image combining section 38 generates a combined image C1 by combining the radiation images, in which body movements have been corrected, to link the radiation images. Note that image combining section 38 generates a combined image C2 by combining the radiation images, in which mechanical errors have been corrected, as necessary.

Figure 17:
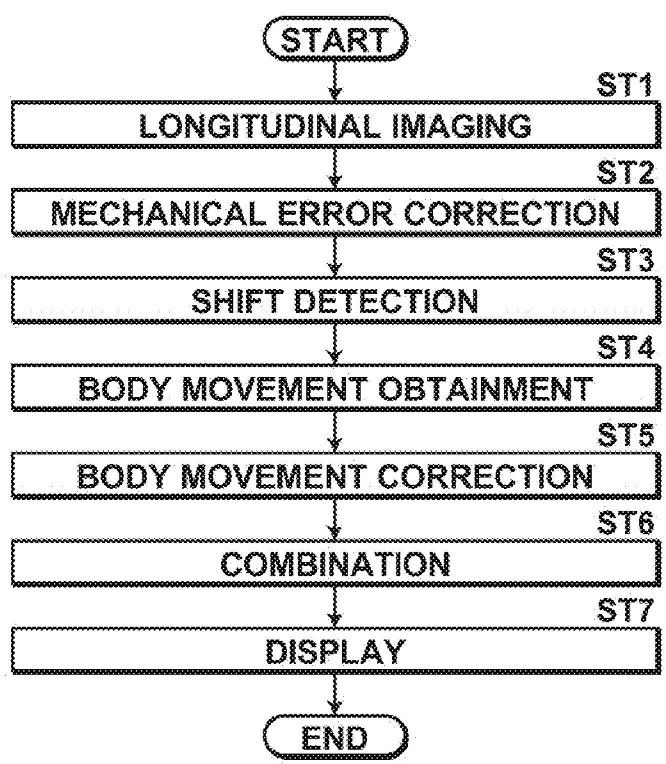
FIG. 17 is a flow chart that illustrates the steps of a process performed by the first embodiment.

Next, the steps of the process performed by the present embodiment will be described. FIG. 17 is a flow chart that illustrates the steps of the process performed by the present embodiment. Note that it is assumed that parameters for executing mechanical error correction are stored in the mechanical error correcting section 34. First, longitudinal imaging is performed while moving the FPD 110, to obtain radiation images at each position along the movement path of the DPF 110 (step ST1). Then, the mechanical error correcting section 34 corrects the mechanical errors within the plurality of radiation images to obtain mechanical error corrected radiation images (step ST2). Next, the shift detecting section 35 detects amounts of shift based on body movements of the subject N within the mechanical error corrected radiation images (step ST3), and further, the body movement obtaining section 36 obtains amounts of body movement based on the amounts of shift (step ST4).

Thereafter, the body movement correcting section 37 corrects the body movements within the mechanical error corrected radiation images to obtain body movement corrected radiation images (step ST5). Next, the image combining section 38 combines the body movement corrected radiation images to generate a combined image C1 (step ST6). Finally, the image display device 60 displays the combined image C1 (step ST7), and the process ends.

Figure 18:
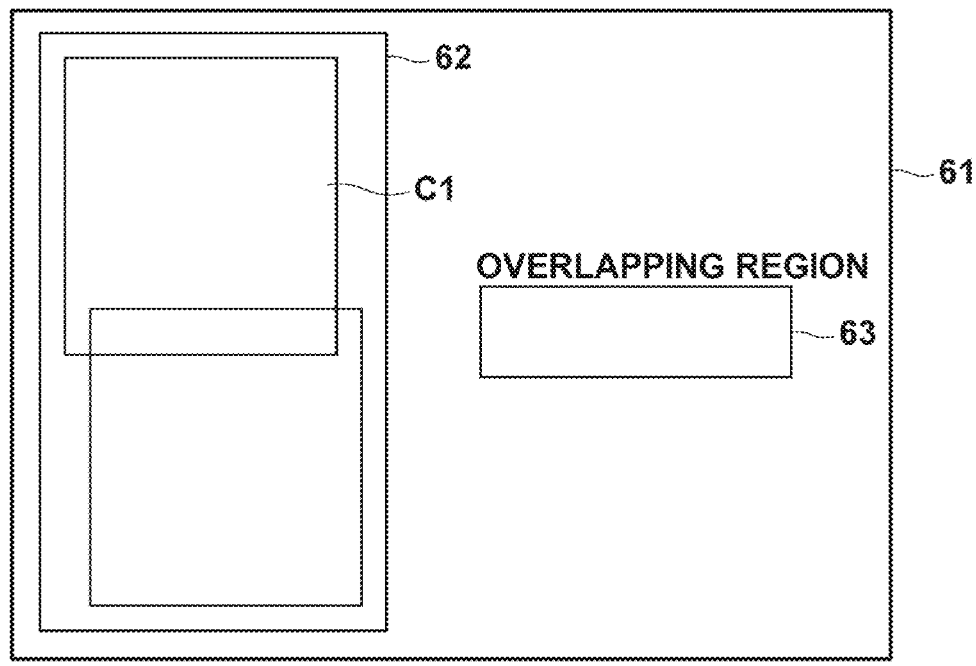
FIG. 18 is a diagram that illustrates an example of the contents of display on a display screen of an image display device.

FIG. 18 is a diagram that illustrates an example of the contents of display on a display screen 61 of the image display device 60. As illustrated in FIG. 18, an image display region 62 in which the combined image C1 is displayed, and an enlarged display region 63 in which the overlapping region of the combined image C1 is enlarged and displayed are displayed on the display screen 61. Here, it is difficult to understand the degree to which body movements have been corrected when the combined image C1 was generated, simply by viewing the combined image C1. For this reason, difference values among corresponding pixel positions are displayed within the overlapping region of the combined image C1. Thereby, in the case that the overlapping region between two images is completely matched, the image of the overlapping region displayed in the enlarged display region 63 will have a density of 0. For this reason, the degree to which the two radiation images are matched in the combined image C1 can be recognized by the density of the image of the overlapping region displayed in the enlarged display region 63.

Note that the two radiation images may be displayed in different colors at the overlapping region instead of displaying the difference values. In this case, the image of the overlapping region displayed in the enlarged display region 63 will be that in which two colors are mixed. For this reason, the degree to which the two radiation images are matched in the combined image C1 can be recognized by the color of the image of the overlapping region displayed in the enlarged display region 63.

Alternatively, correlative values of each pixel position within the overlapping region may be calculated, the size of the correlative values of each pixel position may be represented by color, and the pixel positions may be displayed in colors according to the correlative values in the enlarged display region 63.

Figure 19:
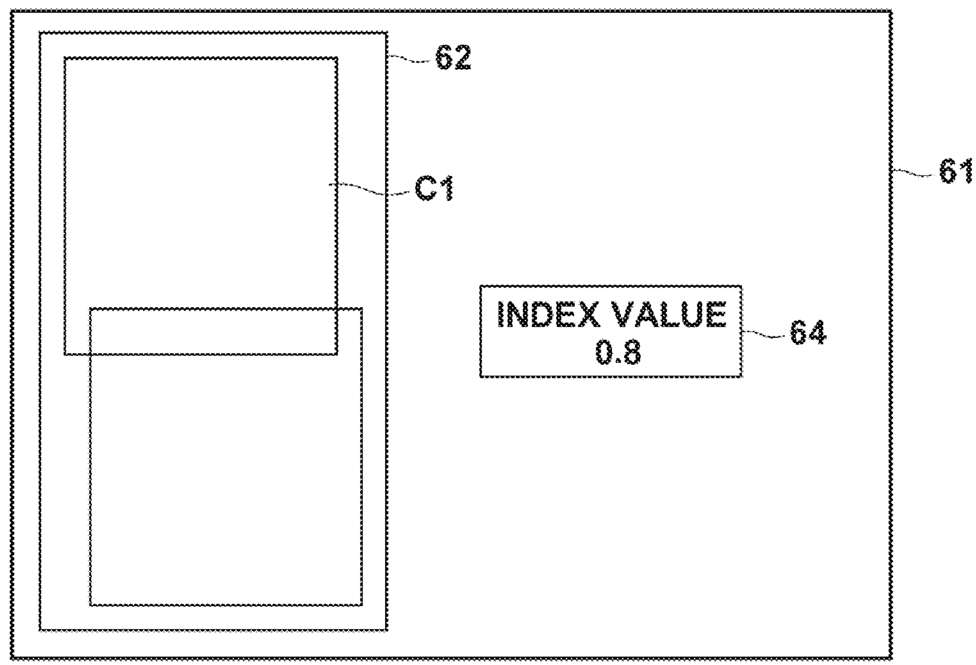
FIG. 19 is a diagram that illustrates another example of the contents of display on a display screen of an image display device.

As a further alternative, an index value display region 64 that displays correlative values of the overlapping region as index values may be displayed on the display screen 61 instead of the enlarged display region 63 as illustrated in FIG. 19. In this case, correlative values may be calculated for each corresponding pixel position. However, FIG. 19 illustrates a case in which a single value, such as a maximum correlative value or an average correlative value, is displayed.

Figure 20:
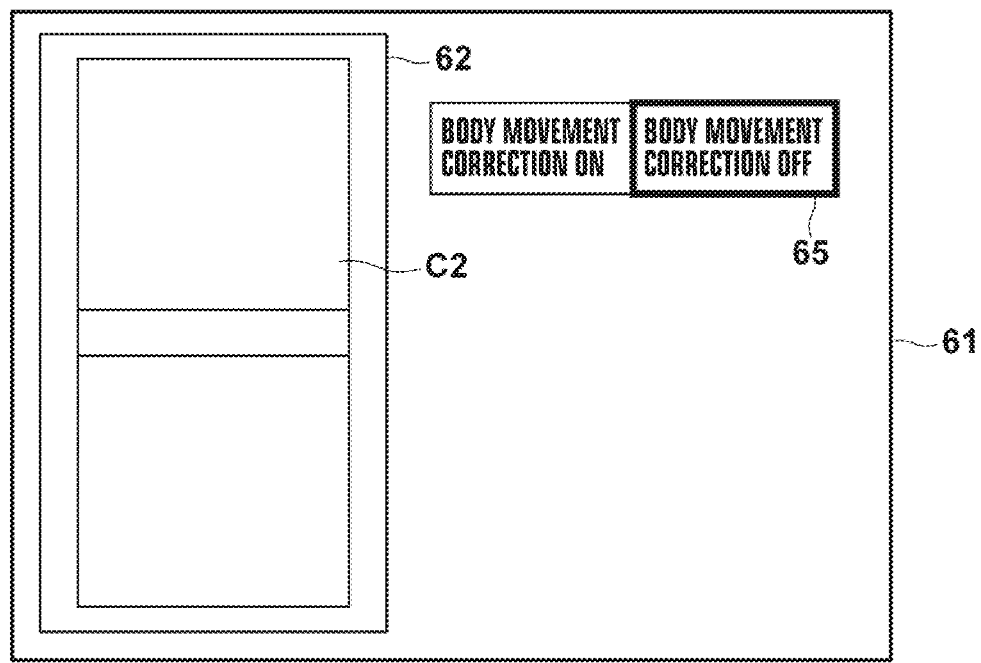
FIG. 20 is a diagram that illustrates still another example of the contents of display on a display screen of an image display device.
Figure 21:
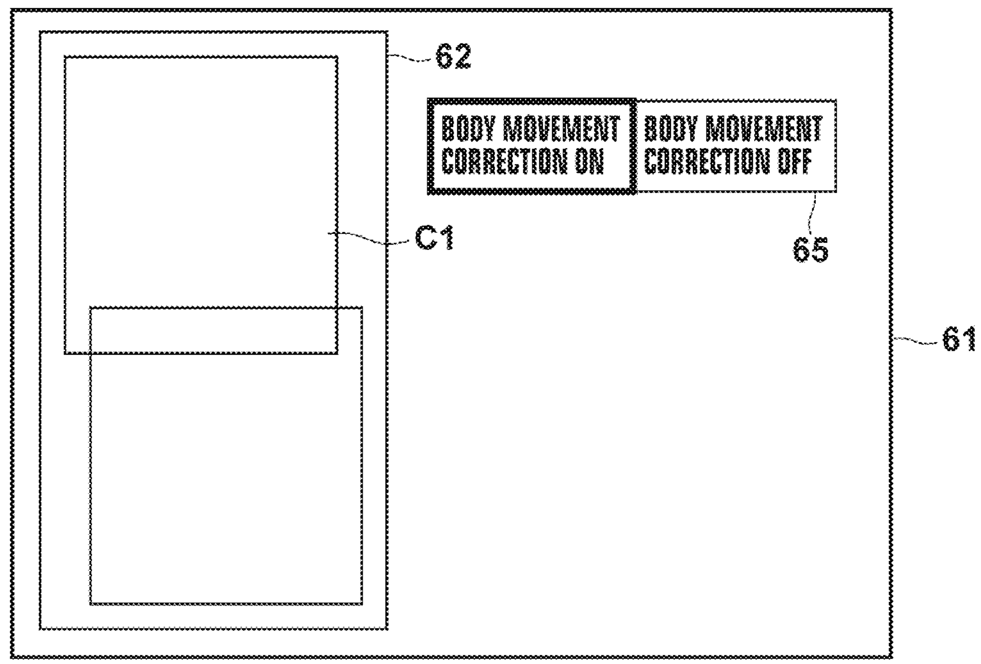
FIG. 21 is a diagram that illustrates still yet another example of the contents of display on a display screen of an image display device.

Further, a configuration may be adopted wherein the combined image C2 is generated by combining the radiation images in which only the mechanical errors have been corrected, and display of the combined image C1, to which body movement correction has been administered, and display of the combined C2 is switched according to operator input. FIG. 20 and FIG. 21 are diagrams for explaining switchable display of the combined image C1 and the combined image C2. First, in the case that the combined image C2, in which body movement has not been corrected, is displayed in the image display region 62 as illustrated in FIG. 20, "BODY MOVEMENT CORRECTION OFF" is selected in a body movement correction ON/OFF display region 65. If an operator switches to display of the combined image C1, the combined image C1, in which body movement has been corrected, is displayed in the image display region 62, is displayed in the image display region 62 as illustrated in FIG. 21, and "BODY MOVEMENT CORRECTION ON" is selected in the body movement correction ON/OFF display region 65. By adopting this configuration, visual recognition of how the combined images C1 and C2 have been corrected with and without body movement correction is facilitated.

In this manner, the present embodiment detects amounts of shift of the subject within mechanical error corrected radiation images and detects amounts of body movement of the subject during imaging operations based on the detected amounts of shift. Therefore, shifts caused by body movements of the subject can be accurately detected.

In addition, the shifts of the subject within the mechanical error corrected radiation images are corrected based on the amounts of body movement, to obtain body movement corrected radiation images. Thereby, the body movement corrected radiation images can be accurately combined to generate a body movement corrected combined image C1. As a result, accurate diagnosis employing the combined image C1 is enabled.

Figure 22:
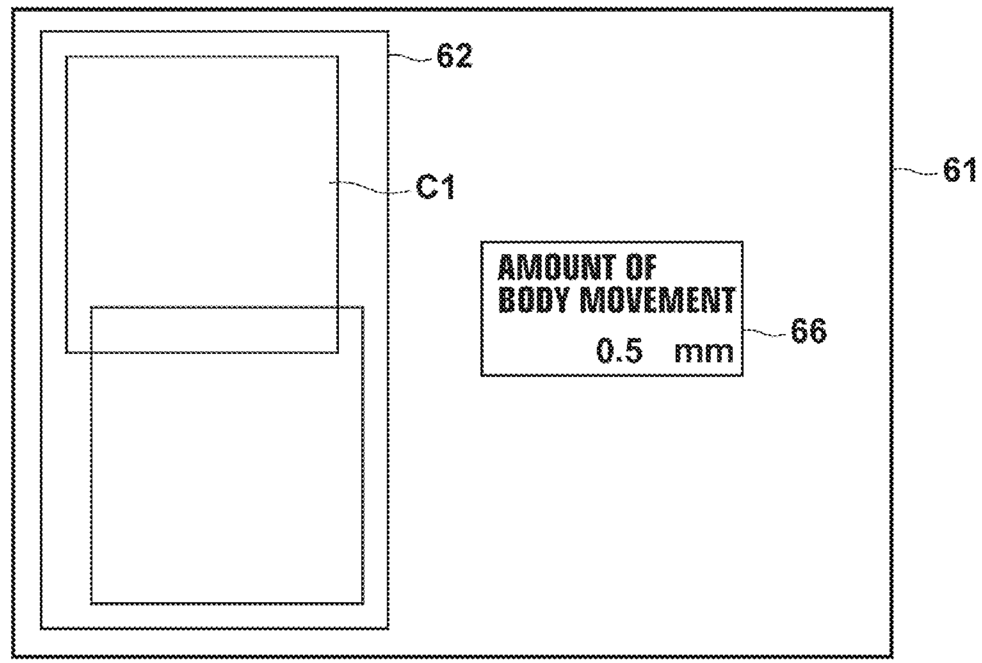
FIG. 22 is a diagram that illustrates another example of the contents of display on a display screen of an image display device.

Note that in the embodiment described above, the amount of body movement may be displayed along with the combined image C1. FIG. 22 is a diagram that illustrates a display screen in which amount of body movement is displayed along with the combined image C1. As illustrated in FIG. 22, the combined image C1 is displayed in the image display region 62 of the display screen 61, and the amount of body movement is displayed in a body movement display region 66. By displaying the amount of body movement, the degree of shift caused by body movement of the subject can be visually recognized.

Figure 23:
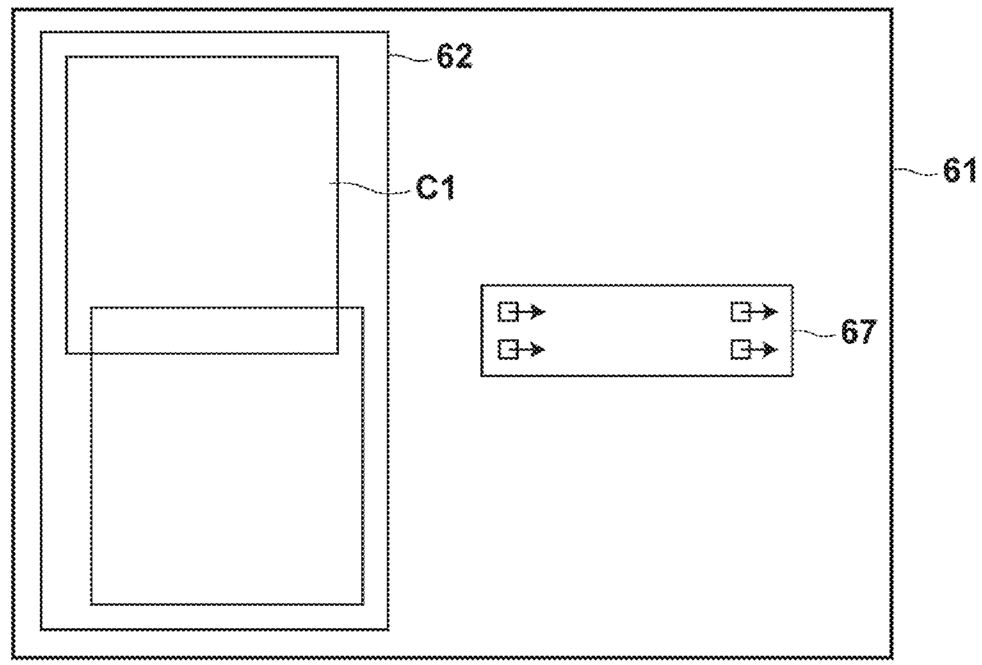
FIG. 23 is a diagram that illustrates still another example of the contents of display on a display screen of an image display device.

In addition, in the case that a plurality of amounts of body movement are calculated, the size and direction of body movement calculated at each position of the template which was utilized during calculation of the amounts of shift may be calculated as body movement vectors, and an optical flow constituted by the body movement vectors may be displayed in an optical flow display region 67 along with the image of the overlapping region of one of the two radiation images, as illustrated in FIG. 23. Note that FIG. 23 illustrates a case in which body movement vectors for four points are displayed. Here, body movement is present in a direction of parallel movement in the combined image C1 illustrated in FIG. 23. Therefore, the optical flow represents parallel movement. Note that the type of body movement which is present can be easily recognized by displaying the optical flow.

FIG. 24 is a collection of diagrams that illustrate examples of optical flow display. In the case that the optical flow is that illustrated in a of FIG. 24, it can be understood that rotational body movement in the counterclockwise direction about a point O1 in the overlapping region is present. In the case that the optical flow is that illustrated in b of FIG. 24, it can be understood that body movement that causes enlargement is present with a point O1 within the overlapping region as its center. In the case that the optical flow is that illustrated in c of FIG. 24, it can be understood that body movement that causes reduction is present with a point O1 within the overlapping region as its center. Note that body movement that causes enlargement and reduction is generated by the subject inhaling and exhaling, for example. In the case that the optical flow is that illustrated in d of FIG. 24, it can be understood that rotational body movement about a point O2 in the overlapping region is present.

By obtaining the optical flow in this manner, it becomes possible to utilize the optical flow in the body movement correcting process administered by the body movement correcting section 37.

A case in which radiation images, in which body movements have been corrected, are combined to generate a combined image and the combined image is displayed has been described above. The apparatus illustrated in FIG. 1 is also equipped with a warning section 39. Hereinafter, a process by which the warning section 39 issues a warning will be described.

The warning section 39 compares the amounts of body movement obtained by the body movement obtaining section 36 at each of a second and subsequent positions during movement of the FPD 110 against a threshold value Th1, and issues a warning when the amount of body movement exceeds the threshold value Th1. Note that a number of pixels corresponding to positioning errors in the case that the FPD 110 is moved (0.5 mm, for example) may be employed as the threshold value Th1. In addition, the warning may be a voice message (including a warning message) or an audio warning. Alternatively, a warning mark or a warning message may be displayed on the display screen of the image display device 60. As a further alternative, warnings may be issued both as sounds and by visual display.

When body movement of the subject N during longitudinal imaging is confirmed by a warning being issued, an operator may operate an emergency stop switch to cease imaging operations. Accordingly, the subject N can be prevented from being unnecessarily exposed to radiation by continuing imaging operations although the degree of body movement is too large to enable images to be combined.

A configuration has been described in which a warning is issued if the amount of body movement of the subject exceeds the threshold value Th1. Alternatively, imaging operations can be automatically ceased when the warning is issued. Thereby, it becomes unnecessary for the emergency stop switch to be operated after the operator confirms the body movement of the subject. In addition, a next imaging operation can be prevented from being executed between the time that the operator confirms the body movement and the time that the operator operates the emergency stop switch. As a result, the subject can be prevented from being unnecessarily exposed to radiation without burdening the operator.

Note that in the embodiment described above, common markers were imaged in all of the overlapping regions of the FPD 110 that is, the overlapping region between positions Q1 and Q2, the overlapping region between positions Q2 and Q3, and the overlapping region between positions Q3 and Q4, and the positions of the markers were detected for each imaging operation. However, the markers may be imaged only at a portion of the above overlapping regions (the overlapping region between positions Q1 and Q2 and the overlapping region between positions Q3 and Q4, for example), and the positions of the markers may be detected only for these overlapping regions. In this case, the positions of the markers in the remaining overlapping regions (the overlapping region between positions Q2 and Q3 in the above example) may be obtained by interpolating the positions of the markers which were actually detected.

In addition, the angles of inclination $\alpha$ and $\gamma$ and displacements $\Delta y$ and $\Delta x$ related to the overlapping regions at which the markers are not imaged may be obtained by interpolating the positions of the markers which were actually detected and the angles of inclination $\alpha$ and $\gamma$ and displacements $\Delta y$ and $\Delta x$ which are obtained based on the actually detected positions of the markers.

In this case, the angles of inclination $\alpha$ and $\gamma$ and displacements $\Delta y$ and $\Delta x$ may vary according to the movement position (panel position) of the FPD 110 due to insufficient precision in the linear slide mechanism that constitutes the moving mechanism 22. Note that FIG. 25 illustrates a case in which the angle of inclination $\alpha$ varies according to the panel position. Therefore, it is desirable for interpolation to be performed taking the properties illustrated in FIG. 25 into consideration, when obtaining the angle of inclination $\alpha$ by interpolation.

In addition, parameters for a transformation process for correcting distortions of images may be calculated from mechanical errors of the imaging surface, such as the angle of inclination $\alpha$ correlated to panel positions. In addition, parameters calculated in this manner may be correlated to panel positions in advance and stored in the memory section of the mechanical error correcting section 34. In this case, calculations are not performed during the transformation process, but parameters correlated to panel positions may be read out from the memory section when panel positions are detected and employed in the transformation process.

Further, a configuration may be adopted, wherein the aforementioned interpolation is not performed, several sets of mechanical errors of the imaging surface, such as the angle of inclination $\alpha$ are obtained then averaged, and the average values are employed as mechanical errors of the imaging surface at all positions of the FPD 110.

A case in which the automatic mechanical error detecting apparatus 80 detects mechanical errors of the imaging surface has been described above. The apparatus of FIG. 1 is also equipped with a user responsive mechanical error detecting apparatus 95. hereinafter, detection of mechanical errors of the imaging surface by the user responsive mechanical error detecting apparatus 95 will be described.

As illustrated in FIG. 1, the user responsive mechanical error detecting apparatus 95 is equipped with: a console 90; an image input section; a corresponding point input section 92; a mechanical error detecting section 93; and a mechanical error storing section 94. The image input section 91, which obtains image data output by the FPD 110, inputs the calibration images CP to the console 90. This input may be performed online in the same manner as in the automatic mechanical error detecting apparatus 80, or offline by recording the calibration images CP onto various disks and then reading out the disks.

The console 90 displays two of the input calibration images CP on an image display device thereof. A user employs the corresponding point input section 92, constituted by a mouse or the like, to input the positions of markers M1 and M2 (refer to FIG. 3, etc.) pictured in the calibration images CP as corresponding points. Note that the two calibration images CP are those obtained by the FPD 110 when the FPD 110 is positioned at two adjacent positions Q1 and Q2, as in the case described previously.

The mechanical error detecting section 93 obtains the angles of inclination $\alpha$ and $\gamma$ and displacements $\Delta y$ and $\Delta x$ based on the positions of the markers indicated by the input corresponding points in the same manner as the mechanical error detecting section 83 of the automatic mechanical error detecting apparatus 80. The angles of inclination $\alpha$ and $\gamma$ and displacements $\Delta y$ and $\Delta x$, which are the mechanical errors of the imaging surface, are recorded and stored in the mechanical error storing section 94. Thereafter, if a command to execute a transformation process is input to the console 90, the console the console reads out the stored mechanical errors EP from the mechanical error storing section 94 and inputs them into the parameter calculating section 84.

Thereafter, parameters are calculated by the parameter calculating section 84 in the same manner as in the case that the automatic mechanical error detecting apparatus 80 is employed as described previously. Further, the mechanical error correcting section 34 administers transformation processes on image data that represent radiation images obtained by normal radiation imaging, based on the calculated parameters. Accordingly in this case as well, shift being present at the boundaries of images can be prevented when the image data which have undergone the above transformation process are combined.

Note that instead of recording and storing the mechanical errors in the mechanical error storing section 94, the parameters calculated by the parameter calculating section 34 may be recorded and stored in the memory means, and read out by the mechanical error correcting section 34 when the above transformation processes are executed.

Figure 26:
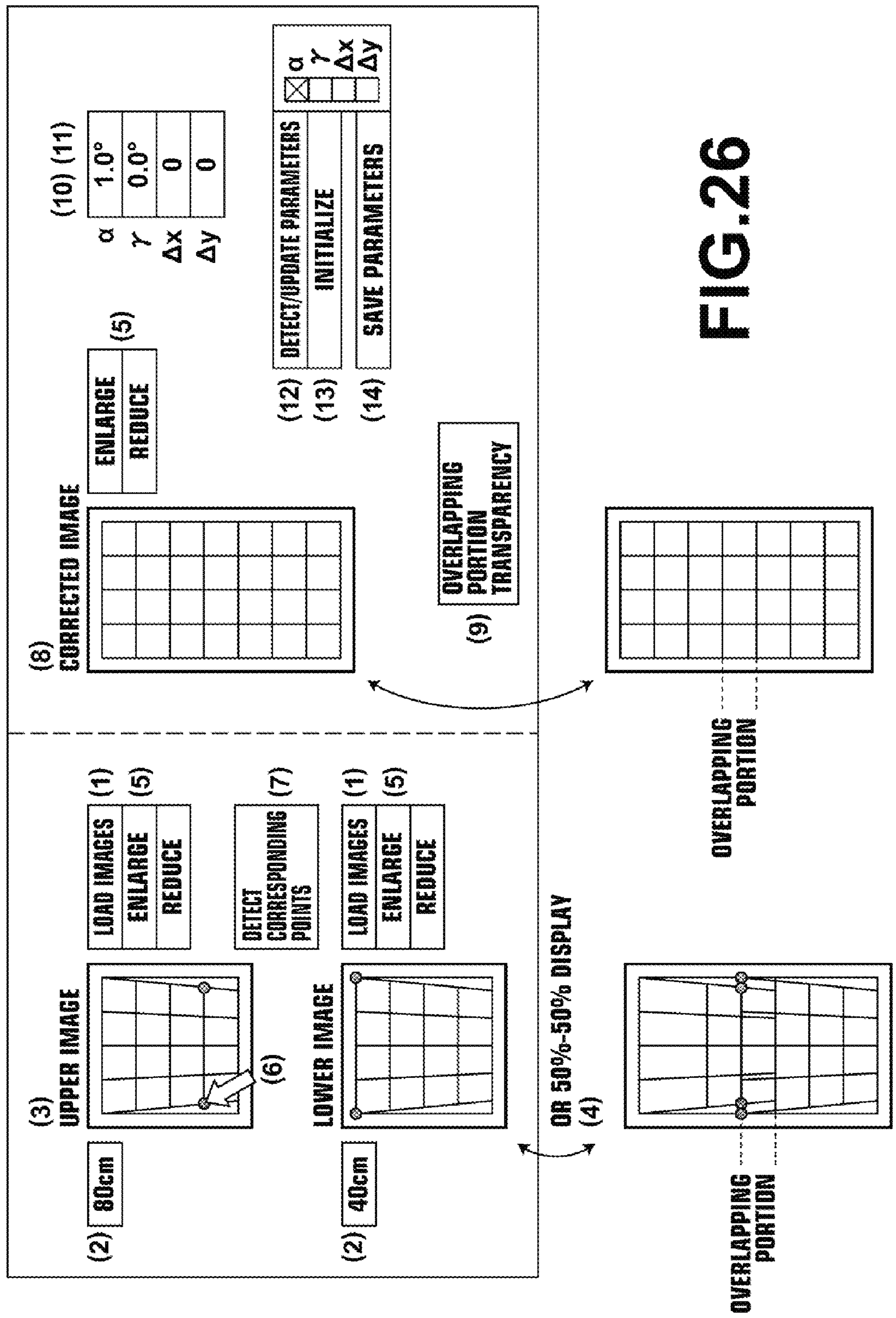
FIG. 26 is a diagram for explaining another embodiment of the present invention.

Next, the functions of the user responsive type mechanical error detecting apparatus 95 will be described in detail with reference to FIG. 26. (1) through (14) listed below are the main functions of the user responsive type mechanical error detecting apparatus 95. FIG. 26 illustrates a display screen for utilizing the above functions (1) through (14), which is displayed on the image display means of the console 90. Hereinafter, how the functions are realized will be described.

Selecting Input Images to be Displayed

An input image is selected by clicking the portion (1) of the display screen with a mouse, and then clicking an ID number or the like of the input images that appear with the mouse.

(2) Displaying Height Position of Imaging Surface Related to Images

The height positions of the imaging surface related to images are displayed in the portion (2) of the display screen.

Displaying the Upper and Lower Images

The upper and lower images are displayed in the portion (3) of the display screen.

Displaying the Overlapping Region of the Upper and Lower Images as 50% of the Upper Image and 50% of the Lower Image This function is a substitute for the function of (3) above. Both the upper and lower images become transparent, and are displayed in an overlapped manner in the portion (4) of the display screen.

Enlarging and Reducing a Displayed Image

Enlarged display or reduced display can be selected by clicking the portion (5) of the display screen with a mouse.

Inputting Corresponding Points within the Upper and Lower Images by Clicks of a Mouse (6) Corresponding points are input by indicating the corresponding points by a cursor or the like as shown in the portion (6) of the display screen, and then clicking the mouse in this state.

(7) Automatically Detecting Corresponding Points, or Automatically Detecting More Specific Corresponding Points within the Vicinities of Input Corresponding Points Corresponding points are detected automatically by clicking the portion (7) of the display screen with a mouse.

(8) Calculating Parameters from Detected Mechanical Errors, and Displaying Images Corrected Using the Parameters The corrected image is displayed in the portion (8) of the display screen.

(9) Selecting Percentages of Transparency of Overlapping Regions in Corrected Images which are Displayed Percentages of transparency which appear by clicking the portion (9) of the display screen with a mouse are clicked again, to select the percentage of transparency. The percentages are 50% for the upper image and 50% for the lower image, for example. The percentage of transparency R for one of the images is selectable within a range from 0% to 100%, and the percentage of transparency of the other image will be (100%−R).

(10) Displaying Mechanical Errors

Mechanical errors are displayed in the portion (10) of the display screen.

(11) Manually Adjusting Mechanical Errors and Reflecting Corrections within Each Image Coordinated with the Manual Adjustments A cursor is placed in the portion (11) of the display screen, and adjustments are performed by rotating the dial of a mouse or the like.

(12) Detecting/Updating Mechanical Errors (Selectable)

Mechanical errors are detected/updated by clicking the portion (12) of the display screen with a mouse or the like.

(13) Initializing Mechanical Errors to Default Values (Selectable)

Mechanical errors are initialized by clicking the portion (13) of the display screen with a mouse or the like.

(14) Saving Detected Mechanical Errors (Selectable)

Detected mechanical errors are saved by clicking the portion (14) of the display screen with a mouse or the like.

One of the four procedures (A) through (D) listed below is adopted to detect mechanical errors of the imaging surface in the user responsive type mechanical error detecting apparatus 95 having the functions listed above.

(A) Automatic Detection of Corresponding Points

Select an input image using function (1)

Automatically detect corresponding points (determine a predetermined range by template matching or the like)

Detect mechanical errors from corresponding points (B) Semiautomatic Detection of Corresponding Points Select an input image using function (1)

Input corresponding points using function (6)

Detect more specific corresponding points within the vicinities of the input corresponding points (determine a predetermined range by template matching or the like)

Detect mechanical errors from corresponding points (C) Manual Input of Corresponding Points Select an input image using function (1)

Enlarge image using function (5)

Input corresponding points at same size magnification using function (6)

Detect mechanical errors from corresponding points (D) Manual Detection of Mechanical Errors Select an input image using function (1)

Match corrected images using function (9) then perform manual detection

A radiation imaging apparatus that performs longitudinal imaging with a subject in an upright position has been described. However, the present invention is not limited to this configuration, and may be applied to a radiation imaging apparatus that performs longitudinal imaging with a subject in a supine position.

The apparatus 150 according to the first embodiment of the present invention has been described above. A program that causes a computer to function as means corresponding to the mechanical error correcting section 34, the shift detecting section 35, the body movement obtaining section 36, the body movement correcting section 37, the image combining section 38 and the warning section 39 to execute the steps of the process illustrated in FIG. 17 is also an embodiment of the present invention. In addition, a computer readable recording medium having such a program stored therein is also an embodiment of the present invention. In these cases as well, reference data may be included within the program or the same recording medium, or supplied by an external apparatus or a separate medium.

Figure 32:
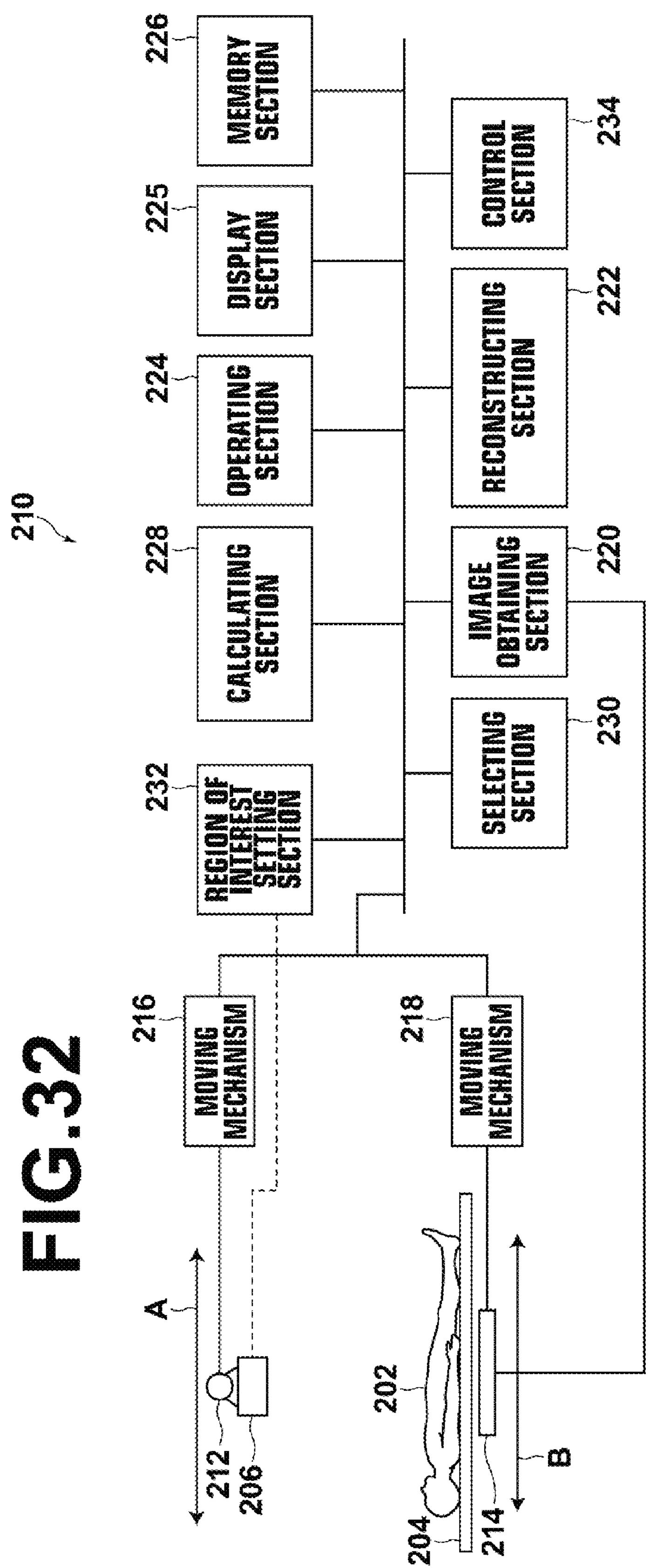
FIG. 32 is a diagram that schematically illustrates an X ray imaging apparatus, to which a radiation imaging apparatus according to a second embodiment of the present invention is applied.
Figure 33:
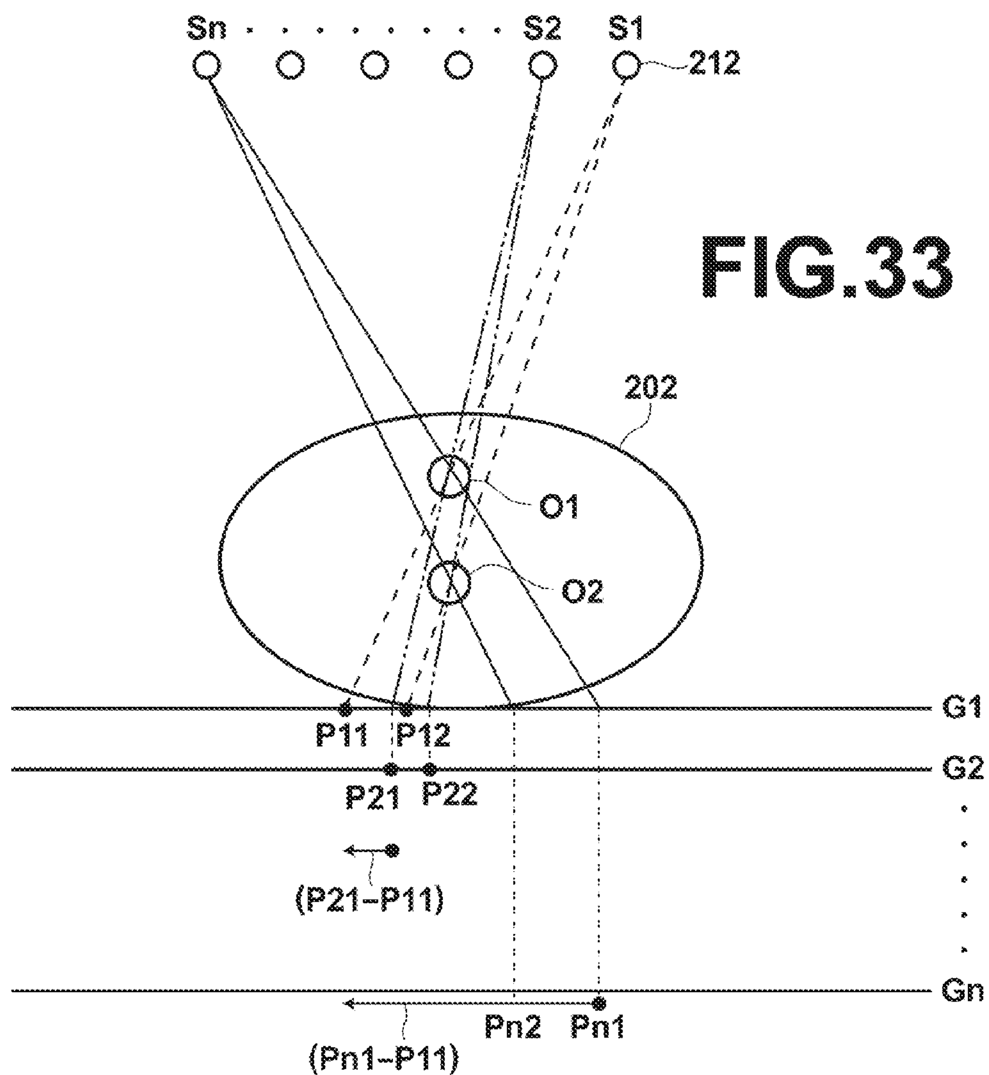
FIG. 33 is a diagram for explaining a tomosynthesis imaging operation.
Figure 34:
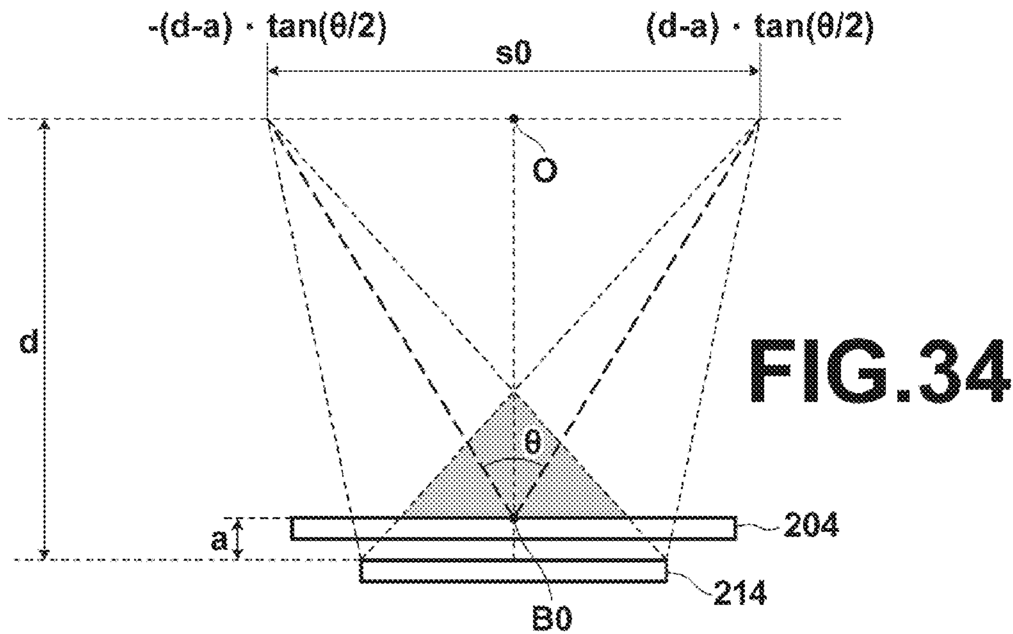
FIG. 34 is a diagram for explaining calculation of the movement range of an X ray tube in the case that the top surface of a top plate of an imaging base of the radiation imaging apparatus is designated as a reference surface.

Next, a second embodiment of the present invention will be described. FIG. 32 is a diagram that schematically illustrates an X ray imaging apparatus 210, to which a radiation imaging apparatus according to a second embodiment of the present invention is applied. FIG. 33 is a diagram for explaining a tomosynthesis imaging operation. FIG. 34 is a diagram for explaining calculation of the movement range of an X ray tube in the case that the top surface of a top plate of an imaging base of the radiation imaging apparatus is designated as a reference surface.

As illustrated in FIG. 32, the X ray imaging apparatus 210 is equipped with: an X ray tube 212; and a flat panel X ray detector 214 (hereinafter, simply referred to as “detector”). The X ray tube is moved either in a linear direction or an arcuate direction by a moving mechanism 216, and irradiates X rays onto a subject 202 on the top plate 204 of the imaging base at a plurality of locations along the movement path thereof. In the present embodiment, the X ray tube is moved linearly in the direction indicated by arrow A. Note that the X ray dosage irradiated onto the subject 202 is controlled to be a predetermined dosage by a control section to be described later. In addition, a collimator 206 (an irradiation field iris) is connected to the X ray tube 212, and the range of the subject 202 onto which X rays are irradiated is capable of being set by an operator.

The detector 214 is placed to face the X ray tube 212 with the top plate 204 of the imaging base on which the subject 202 is placed interposed therebetween, so as to detect X rays which have passed through the subject 202. The detector 214 is moved either in a linear direction or an arcuate direction by a moving mechanism 218, and detects X rays which have passed through the subject at a plurality of locations along the movement path thereof. In the present embodiment, the detector 214 is moved linearly in the direction indicated by arrow B.

In addition, the X ray imaging apparatus 210 is equipped with an image obtaining section 220 and a reconstructing section 222. The image obtaining section 220 moves the X ray tube 212 linearly, irradiates X rays onto the subject 202 from different angles, and detects X rays which have passed through the subject 202 using the detector 214, to obtain a plurality of images at a plurality of positions along the movement path. The reconstructing section 222 reconstructs the plurality of images obtained by the image obtaining section 220 to generate a tomographic image that represents a desired cross section of the subject 202. Hereinafter, the method by which the tomographic image is reconstructed will be described.

As illustrated in FIG. 33, when the X ray tube irradiates the subject 202 at different irradiation angles from each of a plurality of positions S1, S2, . . . Sn, images G1, G2, . . . Gn are obtained. If target objects (O1 and O2) which are present at different depths are projected from the position S1 of the radiation source, the target objects are projected onto the image G1 at positions P11 and P12. If the target objects (O1 and O2) are projected from the position S2 of the radiation source, the target objects are projected onto the image G2 at positions P21 and P22. By repeating projection from the different radiation source positions S1, S2, . . . Sn in this manner, the target object O1 is projected onto positions P11, P21, . . . Pn1 corresponding to each position of the radiation source, and the target object O2 is projected onto positions P12, P22, . . . Pn2.

In the case that it is desired to emphasize the cross section at which the target object O1 is present, the image G2 is moved for a distance (P21-P11), the image G3 is moved for a distance (P31-P11), . . . , image Gn is moved for a distance (Pn1-P11), and the images are added. Thereby, a tomographic image in which structures at the depth of the target object O1 are emphasized is produced. In the case that it is desired to emphasize the cross section at which the target object O2 is present, the image G2 is moved for a distance (P22-P12), the image G3 is moved for a distance (P32-P12), image Gn is moved for a distance (Pn2-P12), and the images are added. Thereby, a tomographic image in which structures at the depth of the target object O2 are emphasized is produced. An image that emphasizes a tomographic image of a desired position can be obtained, by positionally aligning the images G1, G2, . . . Gn and adding the images according to the position of a necessary cross section in this manner.

In addition, the X ray imaging apparatus 210 is equipped with an operating section 224, a display section 225 and a memory section 226. The operating section 224 is constituted by an input device such as a keyboard, a mouse, or a touch panel, and receives input to operate the X ray imaging apparatus 210 from an operator. In addition, the operating section 224 also receives input of desired tomographic angles to determine the range in which tomographic images are obtained. In the present embodiment, the components of the X ray imaging apparatus 210 operate according to information input by an operator through the operating section 224. The display section 225 is a display device such as a liquid crystal monitor, and displays images obtained by the image obtaining section 220, tomographic images reconstructed by the reconstructing section 222, and messages necessary to operate the X ray imaging apparatus 210. The memory section 226 has store therein various parameters which are necessary for the X ray imaging apparatus 210 to operate.

In addition, the X ray imaging apparatus 210 is equipped with a calculating section 228. The calculating section 228 calculates the range of movement of the X ray tube 212 based on the distance between the X ray tube 212 and the reference surface and a desired tomographic angle that employs a reference point on the reference surface as a reference. FIG. 34 is a diagram for explaining calculation of the movement range of the X ray tube 212 in the second embodiment. Note that in FIG. 34, the reference surface is the top surface of the top plate 204 of the imaging base. Here, the top surface of the top plate 204 of the imaging base, the detecting surface of the detector 214, and the movement path of the X ray tube 212 are parallel. Therefore, the shortest distance between the X ray tube 212, the top surface of the top plate 201 of the imaging base, and the detecting surface of the detector 214 along the movement path of the X ray tube 212 is designated as the distance between the X ray tube 212, the top surface of the top plate 201 of the imaging base, and the detecting surface of the detector 214. Note that in the case that the X ray tube 212 moves along an arcuate path, the distance between the cross section, the top surface of the top plate 201 of the imaging base, the detecting surface of the detector 214, and the X ray tube 212 is the furthest distance between the cross section, the top surface of the top plate 201 of the imaging base, the detecting surface of the detector 214, and the X ray tube 212 along the movement path thereof.

Here, in the explanation of FIG. 34, the movement range of the X ray tube 212 is designated as s0, the distance between the X ray tube 212 and the detecting surface of the detector 214 is designated as d, the desired tomographic angle is designated as θ, and the distance between the detecting surface of the detector 214 and the reference surface (that is, the top surface of the top plate 204 of the imaging base) is designated as a. In addition, the intersection of a normal lien that passes through the barycenter of the detector 214 and the reference surface is designated as the reference point B0 on the reference surface. In addition, the desired tomographic angle θ is input via the operating section 224. The desired tomographic angle θ may be input as is, or as an oscillation angle (that is, θ/2). In the present embodiment, the desired tomographic angle θ is input as is.

Based on the relationship illustrated in FIG. 34, the movement range s of the X ray tube 212 can be calculated from the distance d, the distance a, and the desired tomographic angel θ. That is, if the intersection between the normal line that passes through the reference point B0 and the movement path of the X ray tube 212 is designated as an origin O, the distance between the reference surface and the X ray tube 212 will become d−a. Therefore, the calculating section 228 calculates the movement range s0 of the X ray tube 212 as $-(d-a)\cdot\tan(\theta/2)\sim(d-a)\cdot\tan(\theta/2)$. Note that the positions at the two ends of the calculated movement range are determined by the calculation, and portions at which the irradiation range of X rays on the detector 214 in cases that the X ray tube 212 is at the end positions overlap (indicated by gray) can be obtained as reconstructable regions for the tomographic image by the X ray imaging apparatus 210.

In addition, the calculating section 228 calculates body movement evaluation values that indicate the degrees of body movement of the subject. This will be described in detail later.

The X ray imaging apparatus is also equipped with a selecting section 230. The selecting section 230 selects images from among all images obtained by the image obtaining section 220 to generate a tomographic image of a certain cross section, when the reconstructing section 22 generates the tomographic image.

In addition, the X ray imaging apparatus is equipped with a region of interest setting section 232. An operator may employ the operating section 224 to set a range in the depth direction of the subject 202 (for example, a range of heights from the top plate of the imaging base), and set a range within a plane perpendicular to the depth direction using the collimator 206. Note that when the range is set using the collimator 206, visible light is irradiated onto the subject 202 through the collimator 206 instead of X rays. The operator is enabled to set a range within a plane perpendicular to the depth direction using the collimator 206 by adjusting the range onto which the visible light is irradiated onto the subject 202. The region of interest setting section 232 sets a three dimensional region of interest, based on the range in the depth direction of the subject 202 set by the operator using the operating section 224 and the range within the plane perpendicular to the depth direction using the collimator 206. Note that in the case that a region of interest is set, the reference surface is the plane within the region of interest closest to the detecting surface of the detector 214.

Further, the X ray imaging apparatus 210 is equipped with a control section 234 that controls the components of the X ray imaging apparatus 210. The control section 234 controls the components of the X ray imaging apparatus 210 according to commands input via the operating section 224.

Figure 35:
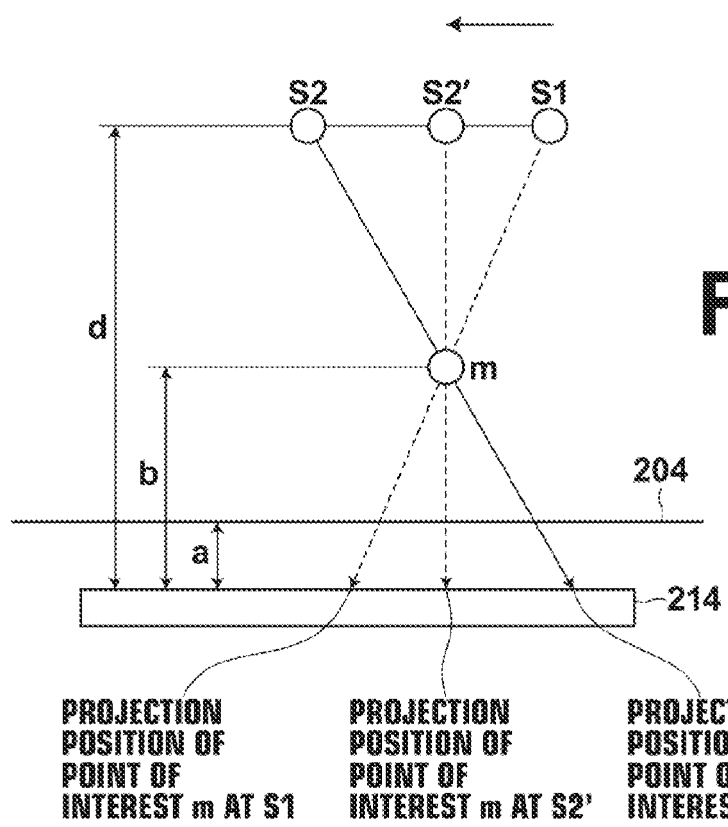
FIG. 35 is a diagram for explaining a method for calculating a body movement evaluation value in the radiation imaging apparatus.

Next, the steps of a process performed by the second embodiment will be described. FIG. 35 is a diagram for explaining a method for calculating a body movement evaluation value in the radiation imaging apparatus 210. Note that here, tomosynthesis imaging, in which the detector 214 is fixed and the X ray tube 212 is moved along a direction parallel to the detector 214, will be described as an example.

When the calculating section 228 calculates a body movement evaluation value, the X ray imaging apparatus 210 of the present invention performs imaging of a phantom (reference subject in) having a known shape, prior to actual imaging of the subject 202. First, the X ray tube 212 is moved according to a predetermined pattern to specify the amounts of movement of the reference subject m within a plurality of images of the reference subject m, which is placed at a known position, obtained by imaging operations. Next, the actual amounts of movement of the X ray tube 212 are calculated based on the amounts of movement of the reference subject.

As illustrated in FIG. 35, when the X ray tube 212 is moved from position S1 to a next position, if the X ray tube 212, which should move to position S2' in the case that there are no mechanical movement errors in the X ray tube 212, is moved to position 82 due to mechanical movement errors, the projection position of the reference subject m within images will be shifted.

However, the distance b between the detecting surface of the detector 214 and the reference subject m and the distance d between the detecting surface of the detector 214 and the X ray tube 212 are known. Therefore, the actual amount of movement of the X ray tube 212 can be calculated based on the interval between the projection position of the reference subject m on the image when imaging is performed at position S1 and the projection position of the reference subject m on the image when imaging is performed at position S2. Note that with respect to the projection positions of the reference subject m on the obtained images, the projection positions can be specified by known methods, such as point of interest extraction and pattern recognition.

In addition, with respect to the actual amount of movement of the X ray tube 212, the method for calculating the actual amount of movement of the X ray tube 212 is not limited to that in which the amount of movement of a reference subject is specified from the distance between projection positions (coordinates within images) in two images obtained by imaging at different imaging positions, and calculating the actual amount of movement of an imaging system (the X ray tube 212 in the present embodiment) based on the amount of movement of the reference subject. The positions of the imaging system can be directly calculated from the projection positions (coordinates within an image) in individual images obtained by imaging from a certain imaging position, and by comparing the positions of the imaging system among a plurality of imaging positions.

The position of the imaging system can be directly calculated from a single image by employing an assembly in which a plurality of markers are arranged with a known positional relationship as reference subjects and obtaining the actual position of the imaging system from the projection positions of the reference subjects (the projection positions of the markers) within a single image, as disclosed in Japanese Unexamined Patent Publication No. 2005-021675 for example, or by other methods.

Providing a sensor that measures the actual position of an imaging system is another example of a method for specifying the position of the imaging system.

Actual imaging of the subject 202 is performed thereafter. Here, first, the X ray tube 212 is moved according to a predetermined pattern, a plurality of imaging operations are executed, and the amounts of movement of the subject 202 within a plurality of images obtained by the imaging operations are specified. The amounts of movement of the subject 202 may be specified in the same manner that the amounts of movement of the reference subject were specified, as explained with reference to FIG. 35. That is, the distance between a projection position of the subject 202 within an image obtained by imaging at position S1 and a projection position of the subject 202 within an image obtained by imaging at position S2 may be measured. Note that with respect to the projection positions of the subject 202 in the obtained images, the projection positions can be specified by known methods, such as point of interest extraction and pattern recognition.

Next, estimated amounts of movement of the subject 202 in the plurality of images obtained by moving the X ray tube 212 for the actual amounts of movement and imaging the subject 202 a plurality of times are calculated. The estimated amounts of movement of the subject 202 can be calculated as described below, because the distance b between the detecting surface of the detector 214 and the subject 202 (which is at the same position as the reference subject m of FIG. 35) and the distance d between the detecting surface of the detector 214 and the X ray tube 212 are known, and it is presumed that the same degree of movement error occurs during movements to each position.

In tomosynthesis imaging, in which imaging is performed while the X ray tube 212 and the detector 214 are moved parallel to each other, the estimated amount of movement of the subject 202 is generally calculated according to Formula (1) below. However, the estimated amount of movement of the subject 202 can be calculated according to Formula (2) below in the present embodiment, because the detector 214 is fixed (actual amount of movement of the detector=0).

$$\text{Estimated Amount of Movement of Subject}=\text{Actual Amount of Movement of Detector}+\text{Actual Amount of Movement of Radiation Source}\cdot(b/(d-b)) \quad (1)$$

$$\text{Estimated Amount of Movement of Subject}=\text{Actual Amount of Movement of Radiation Source}\cdot(b/(d-b)) \quad (2)$$

Finally, a body movement evaluation value that indicates the degree of body movement by the subject 202 can be calculated by calculating the difference between the amount of movement of the subject and the estimated amount of movement of the subject. The body movement evaluation value assumes a value proportionate to the amount of body movement in cases that body movement of the subject 202 is present during actual imaging operations, and assumes a value of 0 in cases that there is no body movement.

The control section 234 receives the body movement evaluation value calculated by the calculating section 228, and displays a warning, such as a message stating "Body movement of the subject was detected. Please perform imaging operations again." following the actual imaging operations in cases that the body movement evaluation value is a predetermined value or greater. At this time, images and points of interest may be enlarged and displayed as a reversible slide show in order to assist confirmation regarding whether additional imaging operations are necessary.

By adopting the configuration described above, body movements of the subject can be accurately detected based on obtained images. In addition, warnings that prompt an operator to perform imaging operations again can be displayed automatically in cases that body movements of subjects are detected. Therefore, improvements in the quality of obtained images can be realized.

Note that the manner in which the body movement evaluation values is utilized is not limited to that described above. Body movements may be monitored during imaging operations, by detecting body movements each time that an imaging operation is completed (or each time that several imaging operations are completed) during the plurality of imaging operations. In this case, the level of body movement may be displayed, warnings may be displayed when the degree of body movement exceeds a predetermined value, or imaging operations may be ceased when the degree of body movement exceeds the predetermined value.

Next, a third embodiment of the present invention will be described. Note that the X ray imaging apparatus according to the third embodiment of the present invention has the same structure as the X ray imaging apparatus 210 of the second embodiment, and only differs in the processes which are performed. Therefore, detailed descriptions of the structures will be omitted here. The X ray imaging apparatus 210 of the third embodiment differs from that of the second embodiment in the method by which the body movement evaluation value is calculated by the calculating section 228.

Figure 36:
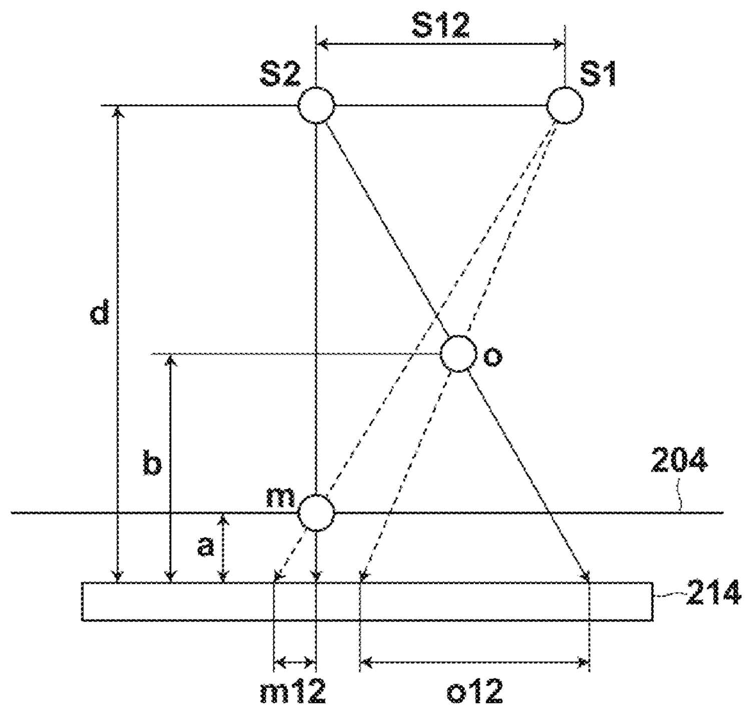
FIG. 36 is a diagram for explaining a method for calculating a body movement evaluation value in a radiation imaging apparatus according to a third embodiment of the present invention.

Hereinafter, the method by which the third embodiment calculates body movement evaluation values will be described. FIG. 36 is a diagram for explaining the method for calculating body movement evaluation values in the X ray imaging apparatus according to the third embodiment.

In the present embodiment, when the calculating section 228 calculates the body movement evaluation value, a marker m (reference subject) having a known shape is placed on the top surface of the top plate 204 of the imaging base during actual imaging of the subject 202, to perform imaging of the reference subject and the subject simultaneously. By adopting this configuration, movement errors of the X ray tube 212 can be reflected during actual imaging of the subject 202. Therefore, body movements of the subject 202 can be detected more accurately compared to the second embodiment described above.

It is preferable for the shape of the marker m (reference subject) to be distinguishable from a feature point o of the subject 202 in images. Examples of feature points o of the subject 202 include bones, organs, branching points of blood vessels, intersecting points of blood vessels, and characteristic portions of anatomical structures that may be employed as markers in images. Alternatively, different markers which are distinguishable from the marker m (by being of a different shape, for example) may be provided to form feature points.

As illustrated in FIG. 36, when X ray tube 212 is moved from position S1 to a next position, if the X ray tube 212 is moved to position S2 due to mechanical movement errors, the projection position of the reference subject (marker m) and the projection position of the feature point o of the subject 202 within images will be shifted.

At this time, the reference subject (marker m) is immobile, and the distance a between the detecting surface of the detector 214 and the reference subject m and the distance d between the detecting surface of the detector 214 and the X ray tube 212 are known. Therefore, the actual amount of movement S12 of the X ray tube 212 can be calculated based on the interval m12 between the projection position of the reference subject m on the image when imaging is performed at position S1 and the projection position of the reference subject m on the image when imaging is performed at position 52.

Next, estimated amounts of movement of the subject 202 in the plurality of images obtained by moving the X ray tube 212 for the actual amount of movement S12 and imaging the subject 202 a plurality of times are calculated. Because the distance b between the detecting surface of the detector 214 and the subject 202 (the feature point o) and the distance d between the detecting surface of the detector 214 and the X ray tube 212 are known, the estimated amounts of movement oa12 (not shown) of the subject 202 can be calculated based on these values.

Finally, a body movement evaluation value that indicates the degree of body movement by the subject 202 is calculated by calculating the difference between the amount of movement of the subject and the estimated amount of movement of the subject. Here, the body movement evaluation value is calculated based on a ratio between the amount of movement m12 of the reference subject (marker m) and the amount of movement o12 of the subject 202 (feature point o).

Specifically, the body movement evaluation value that indicates the degree of body movement by the subject 202 can be calculated by calculating a difference between a ratio r12 (r12=012/m12) between the amount of movement m12 of the reference subject (marker m) and the amount of movement o12 of the subject 202 (feature point o) and a ratio ra12 (ra12=oa12/m12) between the amount of movement m12 of the reference subject (marker m) and the estimated amount of movement oa12. The body movement evaluation value assumes a value proportionate to the amount of body movement in cases that body movement of the subject 202 is present during actual imaging operations, and assumes a value of 0 in cases that there is no body movement. Note that the manners in which the calculated body movement evaluation value is utilized are the same as those in the second embodiment described above.

The same advantageous effects as those obtained by the second embodiment described above can also be obtained by the configuration of the third embodiment.

Radiation imaging apparatuses according to the second and third embodiments of the present invention have been described in detail above. However, the present invention is not limited to the above embodiments.

For example, the above embodiments were described as apparatuses that perform tomosynthesis imaging along a linear trajectory. Alternatively, the present invention may be applied to apparatuses that perform tomosynthesis imaging along arcuate trajectories and precession trajectories. In addition, the present invention may be applied to apparatuses that perform longitudinal combination imaging, energy subtraction imaging, and CT imaging, in addition to tomosynthesis imaging. In these cases, the computational formulas may be changed according to the geometric properties of the movement trajectories of the radiation source and/or the radiation detecting means.

The invention claimed is:

1. A radiation imaging apparatus, comprising:

an imaging means for irradiating radiation;

a radiation detector for detecting the radiation of a subject positioned between the irradiating radiation and the radiation detector; and a moving means for moving the imaging means and/or the radiation detector;

the radiation imaging apparatus being configured to perform a plurality of imaging operations of a subject by moving the imaging means and/or the radiation detector; and the radiation imaging apparatus further comprising:

image obtaining means for reading out signals from the radiation detector each time the radiation detector is moved and the radiation is irradiated, to obtain a plurality of images of the subject;

a mechanical error detecting means for detecting mechanical errors of the imaging means and/or the radiation detector; and body movement obtaining means for obtaining the amounts of body movement of the subject during the imaging operations, based on the mechanical errors obtained by the mechanical error detecting means, wherein the radiation imaging apparatus moves the radiation detector, irradiates radiation which has passed through the subject onto the radiation detector each time that the position of the radiation detector changes by being moved, and obtains a plurality of radiation images, at least portions thereof being overlapped, wherein the imaging means moves the radiation detector along a predetermined axis of movement and irradiates radiation which has passed through the subject onto the radiation detector each time that the position of the radiation detector changes due to the movement and wherein the radiation imaging apparatus further comprises:

a mechanical error correcting means for correcting the mechanical errors in the plurality of radiation images, to obtain mechanical error corrected radiation images; and a shift detecting means, for detecting amounts of shift in the subject among the mechanical error corrected radiation images, and wherein the body movement obtaining means obtains the amounts of body movement of the subject during the imaging operations, based on the amounts of shift, wherein mechanical error includes inclinations of an imaging surface.

2. A radiation imaging apparatus as defined in claim 1, further comprising:

display means for displaying the amounts of body movement.

3. A radiation imaging apparatus as defined in claim 1, further comprising:

a body movement correcting means for correcting the shifts of the subject among the mechanical error corrected radiation images based on the amounts of body movement, to obtain body movement corrected radiation images; and an image combining means for generating body movement corrected combined images, which are the body movement corrected radiation images combined with each other; and the display means being a means for displaying the body movement corrected combined images.

4. A radiation imaging apparatus as defined in claim 3, wherein:

the image combining means generates the body movement corrected combined images such that the degree of positional alignment can be visually confirmed at the portions of the body movement corrected images at which a plurality of the body movement corrected images overlap.

5. A radiation imaging apparatus as defined in claim 3, wherein:

the image combining means further generates mechanical error corrected combined images, which are the mechanical error corrected radiation images combined with each other; and the display means switchably displays the body movement corrected combined images and the mechanical error corrected combined images.

6. A radiation imaging apparatus as defined in claim 1, further comprising:

warning means for issuing a warning in the case that the amounts of body movement exceed a predetermined threshold value.

7. A radiation imaging apparatus as defined in claim 6, wherein:

the imaging means ceases irradiation of the radiation onto the subject in the case that a warning is issued by the warning means.

8. A radiation imaging apparatus as defined in claim 1, wherein:

the mechanical errors is at least one of: inclination of an imaging surface, displacement of the imaging surface from a predetermined position, relative shifting among the plurality of radiation images, and displacement of a subject surface, which is a reference surface of the subject, and the imaging surface in a direction parallel thereto.

9. A radiation imaging apparatus, comprising:

a radiation source for emitting radiation;

a radiation detecting means for detecting the radiation of a subject positioned between the emitting radiation and the radiation detecting means; and a moving means for moving the radiation source and/or the radiation detector;

the radiation source and/or the radiation detector being moved to perform a plurality of imaging operations of a subject; and further comprising:

an imaging system actual movement calculating means, for moving the radiation source and/or the radiation detecting means according to a predetermined pattern, performing a plurality of imaging operations of a reference subject placed at a known position, and for calculating the actual amounts of movement of the radiation source and/or the radiation detecting means based on the projected position of the reference subject within each image obtained by the plurality of imaging operations;

a subject movement specifying means, for specifying the amounts of movement of the subject within a plurality of images, which are obtained by moving the radiation source and/or the radiation detecting means according to the predetermined pattern and performing a plurality of imaging operations;

an estimated subject movement calculating means, for calculating estimated amounts of movement of the subject within a plurality of images which are obtained by moving the radiation source and/or the radiation detecting means according to the predetermined pattern for the actual amounts of movement and performing a plurality of imaging operations; and a body movement evaluation value calculating means, for calculating a body movement evaluation value that indicates the degree of body movement of the subject, based on a difference between the amounts of movement of the subject and the estimated amounts of movement of the subject, a warning being displayed or imagining operations being ceased when the body movement evaluation value exceeds a predetermined threshold value.

10. A radiation imaging apparatus as defined in claim 1, further comprising:

display means for displaying the amounts of body movement;

a body movement correcting means for correcting the shifts of the subject among the mechanical error corrected radiation images based on the amounts of body movement, to obtain body movement corrected radiation images; and an image combining means for generating body movement corrected combined images, which are the body movement corrected radiation images combined with each other; and the display means being a means for displaying the body movement corrected combined images.

11. A radiation imaging apparatus as defined in claim 1, further comprising:

display means for displaying the amounts of body movement; and warning means for issuing a warning in the case that the amounts of body movement exceed a predetermined threshold value.

12. A radiation imaging apparatus as defined in claim 1, further comprising:

display means for displaying the amounts of body movement, wherein the mechanical errors is at least one of: inclination of an imaging surface, displacement of the imaging surface from a predetermined position, relative shifting among the plurality of radiation images, and displacement of a subject surface, which is a reference surface of the subject, and the imaging surface in a direction parallel thereto.

13. A radiation imaging apparatus as defined in claim 1, further comprising:

a body movement correcting means for correcting the shifts of the subject among the mechanical error corrected radiation images based on the amounts of body movement, to obtain body movement corrected radiation images; and an image combining means for generating body movement corrected combined images, which are the body movement corrected radiation images combined with each other;

the display means being a means for displaying the body movement corrected combined images; and warning means for issuing a warning in the case that the amounts of body movement exceed a predetermined threshold value.

14. A radiation imaging apparatus as defined in claim 1, further comprising:

a body movement correcting means for correcting the shifts of the subject among the mechanical error corrected radiation images based on the amounts of body movement, to obtain body movement corrected radiation images; and an image combining means for generating body movement corrected combined images, which are the body movement corrected radiation images combined with each other; and the display means being a means for displaying the body movement corrected combined images, wherein:

the mechanical errors is at least one of: inclination of an imaging surface, displacement of the imaging surface from a predetermined position, relative shifting among the plurality of radiation images, and displacement of a subject surface, which is a reference surface of the subject, and the imaging surface in a direction parallel thereto.

15. A radiation imaging apparatus as defined in claim 1, further comprising:

warning means for issuing a warning in the case that the amounts of body movement exceed a predetermined threshold value, wherein:

the mechanical errors is at least one of: inclination of an imaging surface, displacement of the imaging surface from a predetermined position, relative shifting among the plurality of radiation images, and displacement of a subject surface, which is a reference surface of the subject, and the imaging surface in a direction parallel thereto.

16. A radiation imaging apparatus as defined in claim 1, further comprising:

display means for displaying the amounts of body movement;

a body movement correcting means for correcting the shifts of the subject among the mechanical error corrected radiation images based on the amounts of body movement, to obtain body movement corrected radiation images; and an image combining means for generating body movement corrected combined images, which are the body movement corrected radiation images combined with each other; and the display means being a means for displaying the body movement corrected combined images; and warning means for issuing a warning in the case that the amounts of body movement exceed a predetermined threshold value.

17. A radiation imaging apparatus as defined in claim 1, further comprising:

display means for displaying the amounts of body movement;

a body movement correcting means for correcting the shifts of the subject among the mechanical error corrected radiation images based on the amounts of body movement, to obtain body movement corrected radiation images; and an image combining means for generating body movement corrected combined images, which are the body movement corrected radiation images combined with each other; and the display means being a means for displaying the body movement corrected combined images; and warning means for issuing a warning in the case that the amounts of body movement exceed a predetermined threshold value, wherein:

the mechanical errors is at least one of: inclination of an imaging surface, displacement of the imaging surface from a predetermined position, relative shifting among the plurality of radiation images, and displacement of a subject surface, which is a reference surface of the subject, and the imaging surface in a direction parallel thereto.

18. A radiation imaging apparatus, comprising:

an imaging means for irradiating radiation;

a radiation detector for detecting the radiation of a subject positioned between the irradiating radiation and the radiation detector; and a moving means for moving the imaging means and/or the radiation detector;

the radiation imaging apparatus being configured to perform a plurality of imaging operations of a subject by moving the imaging means and/or the radiation detector; and the radiation imaging apparatus further comprising:

image obtaining means for reading out signals from the radiation detector each time that an imaging operation is performed, to obtain a plurality of images of the subject;

a mechanical error detecting means for detecting mechanical errors of the imaging means and/or the radiation detector; and body movement obtaining means for obtaining the amounts of body movement of the subject during the imaging operations, based on the mechanical errors obtained by the mechanical error detecting means;

a body movement correcting means for correcting the shifts of the subject among the mechanical error corrected radiation images based on the amounts of body movement, to obtain body movement corrected radiation images;

an image combining means for generating body movement corrected combined images, which are the body movement corrected radiation images combined with each other;

the display means being a means for displaying the body movement corrected combined images; and warning means for issuing a warning in the case that the amounts of body movement exceed a predetermined threshold value, wherein mechanical error includes inclinations of an imaging surface.

19. A radiation imaging apparatus as defined in claim 18, wherein:

the imaging means ceases irradiation of the radiation onto the subject in the case that a warning is issued by the warning means.

* * * * *